US 6,296,619 B1

(12) United States Patent
Brisken et al.

(10) Patent No.: US 6,296,619 B1
(45) Date of Patent: Oct. 2, 2001

(54) THERAPEUTIC ULTRASONIC CATHETER FOR DELIVERING A UNIFORM ENERGY DOSE

(75) Inventors: Axel F. Brisken, Fremont; John R. McKenzie, San Carlos; Robert F. Zuk, Atherton; Menahem Nassi, Palo Alto; Mark W. Cowan, Fremont; Paul D. Corl, Palo Alto, all of CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

(21) Appl. No.: 09/223,225

(22) Filed: Dec. 30, 1998

(51) Int. Cl.[7] .............................. A61B 17/20; A61B 8/14
(52) U.S. Cl. .............................................. 604/22; 600/466
(58) Field of Search ................................. 601/2; 600/437, 600/447, 459, 462, 466, 467, 470, 472; 604/20–22, 96.01, 101.01–101.05

(56) References Cited

U.S. PATENT DOCUMENTS

| 4,697,595 | 10/1987 | Breyer et al. ........................ 128/660 |
| 5,197,946 | 3/1993 | Tachibana . |
| 5,240,004 | 8/1993 | Walinsky et al. ............... 128/662.06 |
| 5,630,837 | 5/1997 | Crowley .................................. 601/2 |
| 5,827,313 | 10/1998 | Ream . |
| 5,830,145 | 11/1998 | Tenhoff ................................. 600/463 |
| 5,928,169 | * 7/1999 | Schatzle et al. ........................ 601/2 |
| 5,957,941 | 9/1999 | Ream . |
| 6,001,069 | 12/1999 | Tachibana et al. ...................... 601/2 |
| 6,017,312 | * 1/2000 | Masters ................................ 600/437 |
| 6,019,726 | * 2/2000 | Webb .................................. 600/459 |

FOREIGN PATENT DOCUMENTS

| WO 9627341 | 9/1996 | (WO) . |
| WO 9629935 | 10/1996 | (WO) . |
| WO 9818391 | 5/1998 | (WO) . |
| WO 9848711 | 11/1998 | (WO) . |
| WO 00/18468 | 4/2000 | (WO) . |

OTHER PUBLICATIONS

Machluf et al., "A novel vector for gene transfection using ultrasound energy" (1998) Pediatrics 102(3):844 Abstract No. 43.

* cited by examiner

*Primary Examiner*—Sharon Kennedy
(74) *Attorney, Agent, or Firm*—Townsend and Townsend and Crew LLP

(57) ABSTRACT

A method of treating a target region in a body lumen, said method comprising: directing a uniform dose of ultrasonic energy from an interior of the lumen radially outward over a treatment length of the lumen, wherein the dosage of ultrasonic energy received at any one point along the length varies by no more than plus or minus 6 decibels from that received at any other point along the length.

71 Claims, 28 Drawing Sheets

THERAPEUTIC ULTRASONIC CATHETER FOR DELIVERING A UNIFORM ENERGY DOSE

TECHNICAL FIELD

The present invention relates to therapeutic ultrasound methods and catheter systems.

BACKGROUND OF THE INVENTION

Therapeutic ultrasound systems have proven effective in enhancing transdermal drug delivery, ablating pathological tissue and non-invasively breaking up concretions within the body. To achieve maximum therapeutic benefits, it is desirable to deliver ultrasound energy as directly as possible to the treatment site. Unfortunately, such treatment site may be within a body lumen, such as a vascular site, where numerous problems exist in attempting to direct therapeutic ultrasound. For example, it is difficult to design a sufficiently flexible device to deliver ultrasound energy along the curved tortuous path of the body lumen, especially for narrow diameter body lumens.

Moreover, to deliver maximum therapeutic benefits along a body lumen treatment region, it is desirable to direct a uniform dosage of ultrasonic energy along the length of the lumen with the dosage of the ultrasound energy varying only minimally along the length of the lumen. Delivering a uniform dose of therapeutic ultrasound energy along the length of the body lumen is especially desirable when concurrently using stents in the lumen. When using stents, overstretching of the vascular wall during stent insertion can cause wall tearing and denudation of endothelial cells which can result in an over proliferative healing response. Therapeutic ultrasound following wall injury reduces the formation of obstructive neointimal hyperplasia. A uniform dose of therapeutic ultrasound would reduce the formation of such hyperplasia along the length of the lumen, and in particular along the length of the stent.

It has proven especially difficult to generate such a uniform ultrasonic field along the length of a body lumen due in part to the typically curved path of the lumen and the dimensions of the ultrasound transducers.

Ultrasound systems which are effective in enhancing transdermal drug delivery operate at frequencies around 1MHz, and tend to be quite large due to the large surface area that it is necessary to affect. Such large transducers are not suitably dimensioned for catheter placement into the small lumens of a patient's body. Moreover, smaller transducers which operate at higher frequencies, (such as 10 to 50 MHZ), are not adapted to generate sufficient energy to enhance in vivo drug delivery, or to cause other therapeutic effect, such as reducing the formation of obstructive neointimal hyperplasia after stent implantation. Instead, such small high frequency transducers are limited to diagnostic applications.

For catheter based systems, achieving the optimal size of the ultrasound transducer is problematic since a small catheter mounted transducer is only able to deliver a small amount of ultrasound energy to the patient. Conversely, a larger device, (which would deliver more therapeutic energy), requires a larger transducer which would unfortunately limit the flexibility of the catheter, thus making access difficult in narrow vascular regions.

In addition, a small catheter mounted transducer is adapted to deliver ultrasound only to the region of the lumen immediately adjacent the transducer, for example at the distal tip of the catheter. An additional problem when using a plurality of ultrasound transducers spaced apart along the length of the catheter is the non-uniformity of ultrasound dose delivered since maximum ultrasound will be delivered adjacent the transducers and minimal ultrasound will be delivered at locations equally spaced between adjacent transducers. Accordingly, it is especially difficult to deliver a uniform dose of ultrasound energy along the length of the body lumen.

U.S. Pat. No. 5,197,946 and published PCT Applications WO 96/27341 and WO 98/18391 to Tachibana disclose catheters having an ultrasound transducer at their distal end. Published PCT Application WO 98/48711 to Tachibana discloses a flexible catheter system directed to providing ultrasound for treating long lesions by providing a catheter having a number of separate ultrasound transducers spaced apart therealong. Published PCT Application WO 96/29935 to Crowley discloses a catheter system for tissue ablation having a plurality of annular shaped ultrasonic transducers spaced apart along the length of the catheter.

SUMMARY OF THE INVENTION

The present invention provides methods and systems for treating a target region in a body lumen by delivering a uniform dose of ultrasonic energy from an interior of the lumen radially outward along a portion of the length of the lumen. As will be explained herein, a "uniform" dosage of ultrasound energy corresponds to ultrasound energy producing a uniform biological effect around the circumference of the body lumen. Such uniform biological effects can be generated by mechanical effects related to cavitation, thermal bio-effects related to the absorption of ultrasound energy, radiation pressure forces arising from the absorption and reflection of ultrasound causing tension in the lumen to be equal around its circumference.

In a preferred aspect of the invention, the uniform dosage of ultrasonic energy received at any one point along the length of the lumen varies by no more ±6 decibels. Also in a preferred aspect of the invention, the uniform dosage of ultrasonic energy will be applied over a length greater than the diameter of the body lumen at the treatment site, usually being at least 0.8 cm of the lumen often being at least 1 cm, and sometimes being 2 cm, 3 cm, or longer.

In various aspects of the present invention, one or more ultrasound transducers are used to generate the uniform dose of ultrasound energy.

When using a single ultrasound transducer, the transducer may have an isotropic radiation pattern and be drawn axially through the lumen at a controlled velocity. Alternatively, when using a single non-isotropic ultrasound transducer, the transducer may be drawn axially through the lumen at a controlled velocity, while simultaneously being rotated about the central axis of the catheter at a controlled angular velocity.

When using a plurality of axially spaced apart isotropic transducers, the transducers may be drawn axially through the lumen at a controlled velocity. Alternatively, by dimensioning the axially spaced apart transducers such that they can be placed at a separation distance less than or equal to the diameter of the catheter, a generally uniform emission along the length of the body lumen can be generated without having to axially draw the transducers through the lumen.

When using a plurality of axially spaced apart non-isotropic transducers, the transducers may either be drawn axially through the lumen at a controlled velocity, rotated about the central axis of the catheter at a controlled angular velocity, or some combination thereof.

Preferred shapes for isotropic transducers include cylindrical or annular transducers having their central axes disposed parallel to the central axis of the catheter. A preferred shape for a non-isotropic transducer is a rectangular bar shaped transducer. Other non-isotropic shapes are also possible including cubic or octagonal shapes, parallel bar shapes or composite structures.

Preferred dimensions of the cylindrical, annular, rectangular or cubic transducers as set forth herein will cause the transducers to operate at resonance, thereby increasing the net therapeutic effect to the body lumen by providing maximum ultrasound energy.

When using a plurality of axially spaced apart transducers, the transducers can be operated in phase so as to cause tissue displacements in directions normal to a central axis of the lumen. Alternatively, the plurality of spaced apart transducers can be operated such that successive transducers are 180° out of phase with one another such that ultrasound energy causing tissue shear displacement along the length of the lumen is produced.

Specifically, when using a plurality of either rectangular bar shaped or cylindrical transducers, (with the transducers being positioned with their electroded surfaces either parallel to, or perpendicular to, the catheter central axis), the polarities of respective transducers can be alternated such that as a first transducer expands in the axial direction, adjacent transducers positioned on either side will simultaneously contract in the axial direction. The axial expansion of the first transducer will create a radial contraction, thereby creating a negative acoustic emission in the radial direction. Simultaneously, the adjacent transducers on either side of the first transducer will contract axially and expand radially, thereby creating a positive acoustic emission in the radial direction. As such, successive transducers will generate alternating negative and positive radial emissions along the length of the catheter. Therefore, a radial acoustic emission field will be generated about the catheter which causes tissue shear displacement along the length of the lumen. An advantage of such a longitudinal shear emission field is that maximal effects will appear close to the catheter surface, (due to the fact that the alternating positive and negative pressure fields would tend to cancel one another out at progressively greater distances from the catheter surface). An additional advantage of this arrangement is that it limits the propagation distance of strong acoustic fields.

Alternatively, should successive transducers be aligned with polarities in the same direction, such that they operate together in phase, each of the successive axially spaced apart transducers will simultaneously emit either a positive or a negative acoustic emission in a radially direction. Therefore, an acoustic field having a generally even strength will be generated along the length of the catheter to cause tissue displacement in radial directions normal to a central axis of the lumen. Using this arrangement, however, it may be preferable to position acoustic insulators between adjacent transducers so as to reduce vibrational interference in the axial direction. The drop in acoustic output in the gaps between individual transducers will preferably be less than or equal to the limits set forth above.

In another aspect of the invention, when using non-isotropic rectangular bar shaped transducers, two or three of the four sides which are disposed parallel to the central axis of the catheter can be acoustically insulated (for example, with an air gap or other acoustic reflective material) such that ultrasound energy emission therefrom is blocked. By blocking ultrasound emission from two or three sides of the rectangular bar shaped transducer, ultrasound energy can be concentrated in one, or alternatively two, unblocked surfaces, thereby emitting ultrasound in directions normal to the central axis of the catheter, thereby increasing the dosage of ultrasound received by the body lumen. Rotation, and/or translation of the non-isotropic rectangular bar shaped ultrasound transducers at controlled velocities through the body lumen provides a uniform dose of ultrasound energy along the length of the body lumen.

By translating and/or rotating the present multi-transducer ultrasonic catheter systems, ultrasound energy can be evenly applied in a uniform dose along a portion of the body lumen in conjunction with the delivery of therapeutic agents along the body lumen.

As will be explained, an additional advantage of employing a plurality of spaced apart transducers is that, when axially translating the catheter to provide a uniform dose of ultrasound, it is only necessary to translate the catheter a distance equal to one half the spacing distance between adjacent transducers.

When employing a plurality of spaced apart ultrasound transducers, the present catheter systems deliver a larger amount of therapeutic ultrasound energy to the patient than could be achieved with a single small transducer. Using a number of small spaced apart ultrasound transducers, the present ultrasonic catheter systems are highly flexible and are thus able to access narrow body lumens. Advantageous applications of the present systems include administering ultrasonic energy for clot lysis, for drug delivery, to augment gene therapy (as described in detail in copending application Ser. No. 09/223,231, the full disclosure of which is incorporated herein by reference), to prevent obstructive neointimal hyperplasia (as described in detail in copending U.S. Pat. No. 6,210,393, issued Apr. 3, 2001, the full disclosure of which is incorporated herein by reference), and/or to inhibit proliferation of smooth muscle cells.

The catheter bodies of the present catheter systems will preferably contain at least two lumens, one for passing electrical leads to the transducer elements and one for positioning a guidewire therethrough. Additional lumens are added in various aspects of the present invention for the delivery of drugs, the inflation of balloons, and/or the evacuation of fluids from the vascular channel, as will be explained.

When using rectangular bar or cylindrical shaped transducers, the individual ultrasound transducers will preferably comprise single crystal piezoelectric materials, polycrystalline piezoelectric ceramic materials, electrostrictive or magnetostrictive materials. In a preferred aspect of the invention, the transducers are operated at a frequency in the range of 100 KHz to 5.0 MHZ.

When using a plurality of axially spaced apart non-isotropic rectangular bar shaped transducers, ultrasound energy will be emitted more strongly in certain radial directions perpendicular to the flat surfaces of the transducers which are parallel to the central axis of the catheter. To achieve a uniform dose of therapeutic ultrasound energy around and along the length of the body lumen, systems are provided to rotate the catheter about its central axis at a controlled angular velocity and to axially translate the catheter along its central axis at a controlled velocity.

In a preferred aspect, when using a plurality of axially spaced apart non-isotropic rectangular bar shaped transducers, the successive transducers can be positioned so as to be rotated about the longitudinal catheter axis with respect to one another. As such, an extended catheter which emits ultrasound energy in a number of different radial directions along its length is produced. By axially displacing the catheter through a body lumen at a controlled velocity, (without rotating the catheter about its central axis), a uniform dose of therapeutic ultrasound energy can also be directed along the length of the body lumen.

Alternatively, however, by rotating such a catheter at a controlled angular velocity, therapeutic ultrasound energy can also be directed radially around the circumference of the body lumen when the successive ultrasound transducers are spaced sufficiently close together. In such a case, rotation of the catheter at a controlled radial velocity about its central axis will provide a uniform dose of therapeutic ultrasound energy, without the need for axially displacing the catheter along the length of the body lumen.

In various aspects of the invention, the non-isotropic rectangular bar shaped transducers are positioned such that their electroded surfaces are parallel to the central longitudinal axis of the catheter. An advantage of positioning the electroded surfaces parallel to the central axis of the catheter is that a more non-isotropic emission pattern is generated. Specifically, in the case of rectangular bar transducers having electroded surfaces disposed parallel to the longitudinal axis of the catheter, a "cloverleaf" non-isotropic acoustic emission field will be generated which is strongest in the four directions perpendicular to the four transducer faces which are disposed parallel to the longitudinal axis of the catheter. There will be nulls in the acoustic emission field in the four diagonal directions which dissect the perpendicular directions. Such a cloverleaf acoustic field will be generated due to the fact that displacements with respect to non-electroded surfaces will be 180° out of phase with respect to the displacement of the electroded surfaces. Strong emissions will emanate from the four orthogonal tranducer faces while the vibrations will cancel on the diagonals between adjacent transducer faces. As such, a stronger amount of ultrasound energy, (corresponding to the "leaves" of the cloverleaf can be directed in preferred directions towards the body lumen. Translation and rotation of the transducers provides a uniform dose of ultrasound along the length of the body lumen.

In other preferred aspects, one or more rectangular bar transducers are positioned such that their electroded surfaces are instead perpendicular to the longitudinal axis of the catheter. An advantage of positioning electroded surfaces perpendicular to the longitudinal axis is that a greater emission symmetry around the body of the catheter will be generated, yielding a generally more isotropic dose of the ultrasound energy to be received by the body lumen. Translation and rotation of the transducers provides a uniform dose of ultrasound along the length of the body lumen.

When using a plurality of cylindrical shaped isotropic ultrasound transducers, the longitudinal axis of each cylindrical transducer and the longitudinal axis of the catheter are parallel and generally co-linear.

Electrodes are attached to opposite surfaces of each cylindrical shaped transducer. The electroded surfaces are disposed either parallel to, or perpendicular to, the central longitudinal axis of the catheter. Specifically, the flat ends of the cylinder, (perpendicular to the catheter central axis), may be used as the opposite electroded surfaces. Alternatively, a central bore can be cut through each of the cylindrical transducers with the inner and outer curved surfaces, (parallel to the central axis), serving as the electroded surfaces.

When using one or more cylindrical shaped transducers with the opposite electroded surfaces being the flat ends of the cylinder or the curved inner and outer surfaces of the cylinder, a generally isotropic radially extending acoustic emission symmetry about the catheter will be achieved. The lower frequency length mode resonance is favored by having electrodes disposed on the ends of the cylinder perpendicular to the central axis of the catheter, which allows greater penetration of the ultrasound energy and which may enhance gene transfection and liopfection, Ser. No. 09/223.231. The lower frequency cylindrical mode resonance and higher frequency thickness mode resonances may also be used. Conversely, circumferential electrodes (i.e.: electroded surfaces disposed on the curved inner and outer surfaces parallel to the central axis of the catheter), favor the higher frequency thickness mode resonance, which can generate relatively large amounts of thermal energy. The length and cylindrical excitation modes can also be used.

In both the case of rectangular bar and of cylindrical shaped transducers, a central longitudinally extending bore can be cut through the transducer, thereby providing access for a positioning wire therethrough. Alternatively, in the case of rectangular bar transducers, a lumen can be placed along one side of the bar to receive a guidewire without significantly affecting the resonant characteristics of the bar itself.

When using a plurality of either rectangular bar shaped or cylindrical transducers, the transducers will also radiate ultrasound energy in a direction along the axial length of the catheter. By spacing the transducers by a distance equal to $(n+0.5)\ \lambda$, where n is an integral number, they can be set to interfere constructively with one another, thereby enhancing the effectiveness of the ultrasound delivery.

The present invention also provides systems for delivery of a uniform dose of therapeutic ultrasound energy comprising a thin polymer or copolymer film ultrasound transducer wrapped around a portion of the length of the outer surface of the catheter. As used herein, the phrase "copolymer film transducer" shall include all polymer and copolymer films. An important advantage of such a copolymer film ultrasound transducer is that it delivers ultrasound in a radially outward direction along its length. As such, it is not necessary to either rotate or translate the catheter to deliver a uniform dose of ultrasound energy along the length of the body lumen.

Being isotropic, the ultrasonic emission from the copolymer film transducer is longitudinally uniform over the length of the copolymer transducer and is also uniform radially around the circumference of the transducer. Due to the polymeric nature of the transducer material, the transducer is itself advantageously flexible adding to the flexibility of the catheter system. Yet another important advantage of the wrapped copolymer film ultrasound transducer is its minimal thickness, making it ideally suitable for insertion into stents. When positioning stent struts against the vascular wall to reduce restenosis, over stretching of the vascular wall can result in a proliferative healing response. Therapeutic ultrasound following wall injury has been shown to substantially reduce and possibly eliminate the formation of obstructive neointimal hyperplasia.

By folding the thin copolymer film over upon itself prior to it being wrapped around the catheter, both the positive and the negative ends of the copolymer film can be disposed on opposite sides of the surface of the catheter system for attachment to electrodes such that a negative electrode contacts only the negative end of the copolymer film and a positive electrode contacts only the positive end of the copolymer film. Alternatively, the positive and negative ends of the copolymer film transducer can both be disposed inside the catheter body providing a smooth exterior surface with no edges which might snag on catheter delivery hardware or which might irritate patient tissues.

In yet another aspect of the present invention, combined ultrasound therapy and imaging systems are provided, both with and without enhanced drug delivery or gene transfection. In preferred aspects, one or more non-isotropic ultrasound transducers are used to direct ultrasound in one or more directions normal to the central axis of the catheter and thereby into the wall of the body lumen as described above. Rotation and translation of the catheter in the body lumen causes the imaging transducer to image the length and circumference of the body lumen concurrently with the one or more therapeutic ultrasound transducers delivering a uniform dose of therapeutic ultrasound along the body lumen.

The present invention also provides systems for controlled delivery of therapeutic agents into body lumens. Specifically, various balloon systems provide a protected and controlled release of a therapeutic agent along a region of the lumen while the present ultrasound transducer or transducers apply therapeutic ultrasound energy along the same region of the lumen into which the therapeutic agent has been released. The present balloon systems operate to seal off a portion of the lumen proximal the ultrasound transducer or transducers for release of a therapeutic agent therein. In addition, balloon systems are provided for selectively retrieving unused drug therapeutic agents after the therapeutic agents have been released into the lumen. Accordingly, after the therapeutic agent has been released to the blocked off portion of the lumen, unused amounts of the therapeutic agents can be easily retrieved.

In preferred aspects, a sheath is used to separate the balloon systems disposed at the exterior of the catheter system from the axially translating and/or rotating transducers disposed therein such that the transducers can be moved while the balloon system remains fixed in position, thereby blocking off the portion of the body lumen which is simultaneously treated by ultrasound energy and therapeutic agent delivery.

In summary, the present invention provides a variety of systems for delivering a uniform dose of therapeutic ultrasound energy along a body lumen. Systems accomplishing this result using one or more therapeutic transducers are set forth. Preferred transducer geometries for operating the transducers at resonance are also disclosed. Systems for axially translating and/or rotating the transducers at controlled velocities to deliver uniform ultrasound are set forth. Systems are provided using both isotropic and non-isotropic ultrasound transducers. Systems for operating successive axially spaced apart transducers in phase or 180 degrees out of phase to achieve either radial tissue compression displacement or axial tissue shear displacement, respectively, are also provided. Systems for blocking the ultrasound energy from certain surfaces of the ultrasound transducers so as to concentrate ultrasound energy in other preferred radial directions, thereby increasing the intensity of ultrasound delivery, are also disclosed.

Systems for delivering a uniform isotropic ultrasound dose without rotation or translation of the catheter using a thin copolymer ultrasound transducer wrapped around the length of a portion of the catheter are also set forth. Systems comprising imaging transducers used in conjunction with the preferred therapeutic transducers are also set forth. Balloon systems for controlled delivery and removal of therapeutic agents are also set forth.

DESCRIPTION OF THE SPECIFIC EMBODIMENTS

Ultrasonic Catheter Systems Comprising Rectangular Bar Shaped Transducers

Figure 1A:
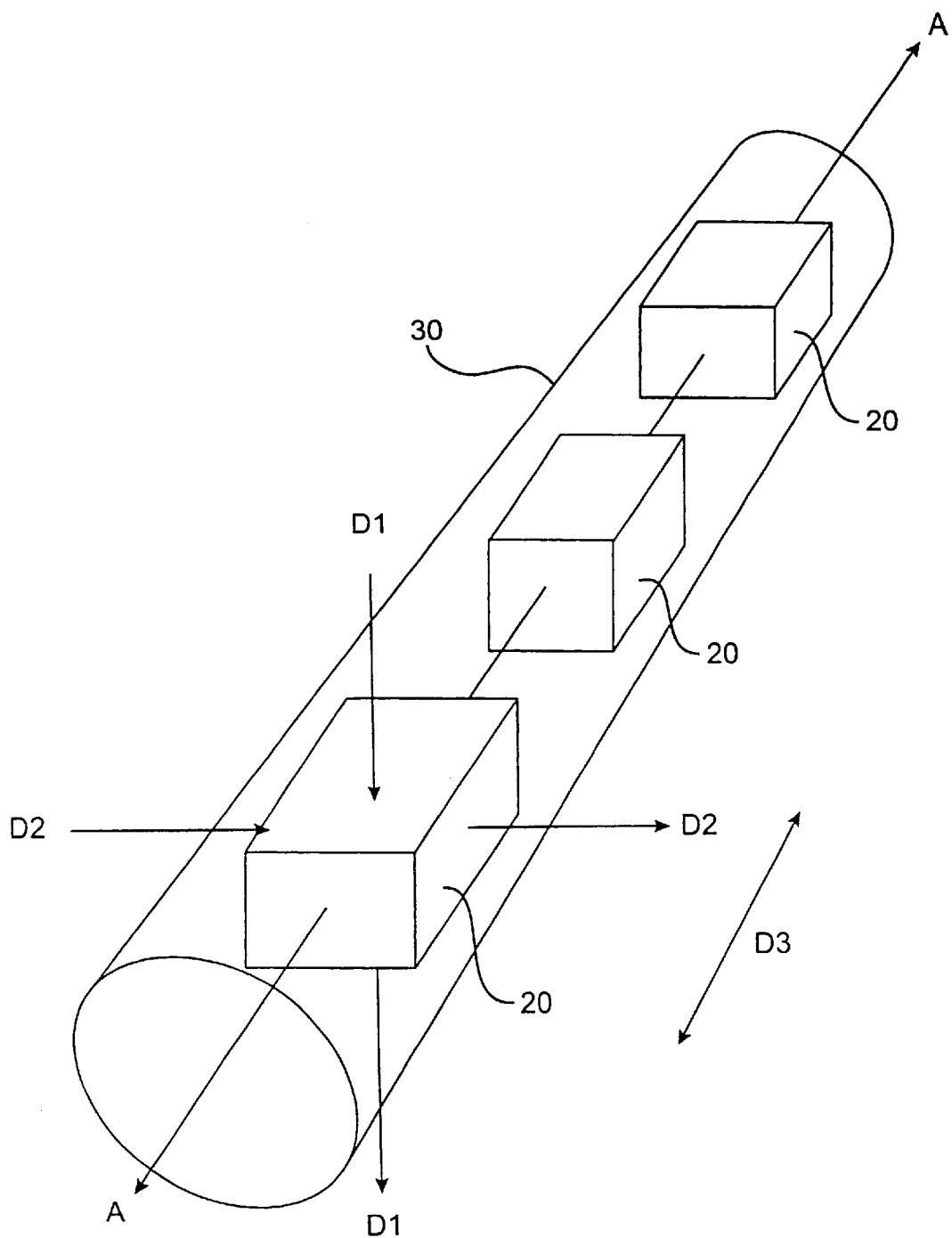
FIG. 1A is a schematic view of a plurality of rectangular bar shaped ultrasound transducers disposed along the longitudinally extending central axis of a catheter.

As is shown schematically in FIG. 1A, a plurality of axially spaced apart rectangular bar shaped transducers 20 are disposed along the longitudinal axis A of a catheter 30. It is, however, to be understood that in alternative aspects of the invention, only one transducer 20 need be used. Accordingly, the schematic representation of FIG. 1A also illustrates the aspect of the present invention where catheter 30 comprises only one ultrasound transducer 20.

Ultrasound energy emitted by transducers 20 in directions D1 and D2 will be emitted in a radial direction perpendicular to the central longitudinal axis A of the catheter, as shown, and thus will be applied directly to the walls of a body lumen into which catheter 30 is received. Energy emitted in direction D3 will be emitted parallel to axis A of the catheter, as shown.

Figures 1A, 1B:
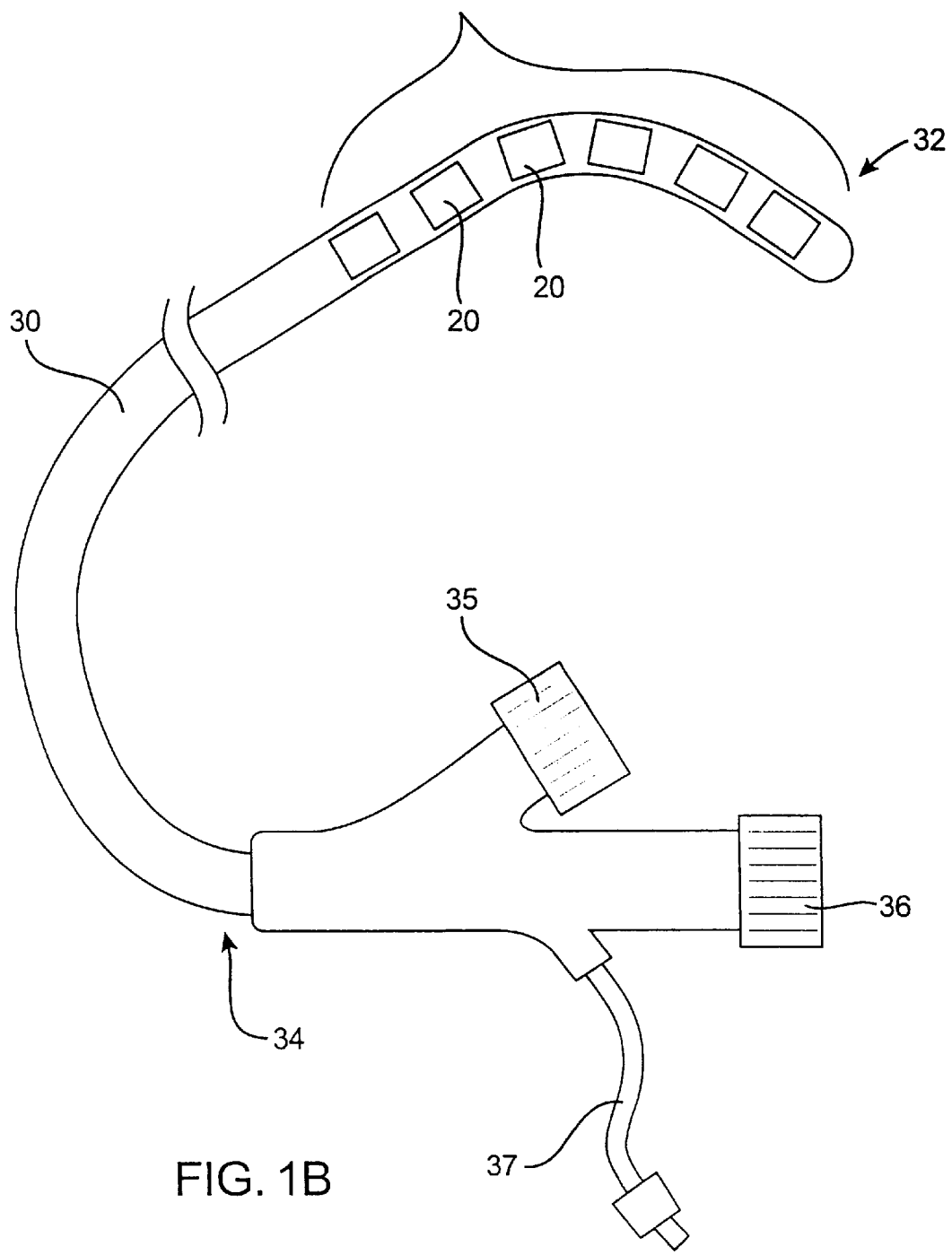
FIG. 1B is a schematic view of a catheter system corresponding to FIG. 1A.

As seen in FIG. 1B, the transducer arrangement shown in FIG. 1A can be incorporated into a catheter system comprising a catheter 30 having a distal end 32 and a proximal end 34. Proximal end 34 preferably comprises a flush port 35, guidewire port 36, and electrical connector 37. In the catheter body 30 itself, lumens for running electrical leads to the transducer 20 and also for receiving a guidewire are also preferably included. As will be explained, additional lumens for the delivery of drugs, the inflation of balloons and/or the evacuation of fluids may also be provided.

Rectangular Bar Shaped Transducers

Figure 2:
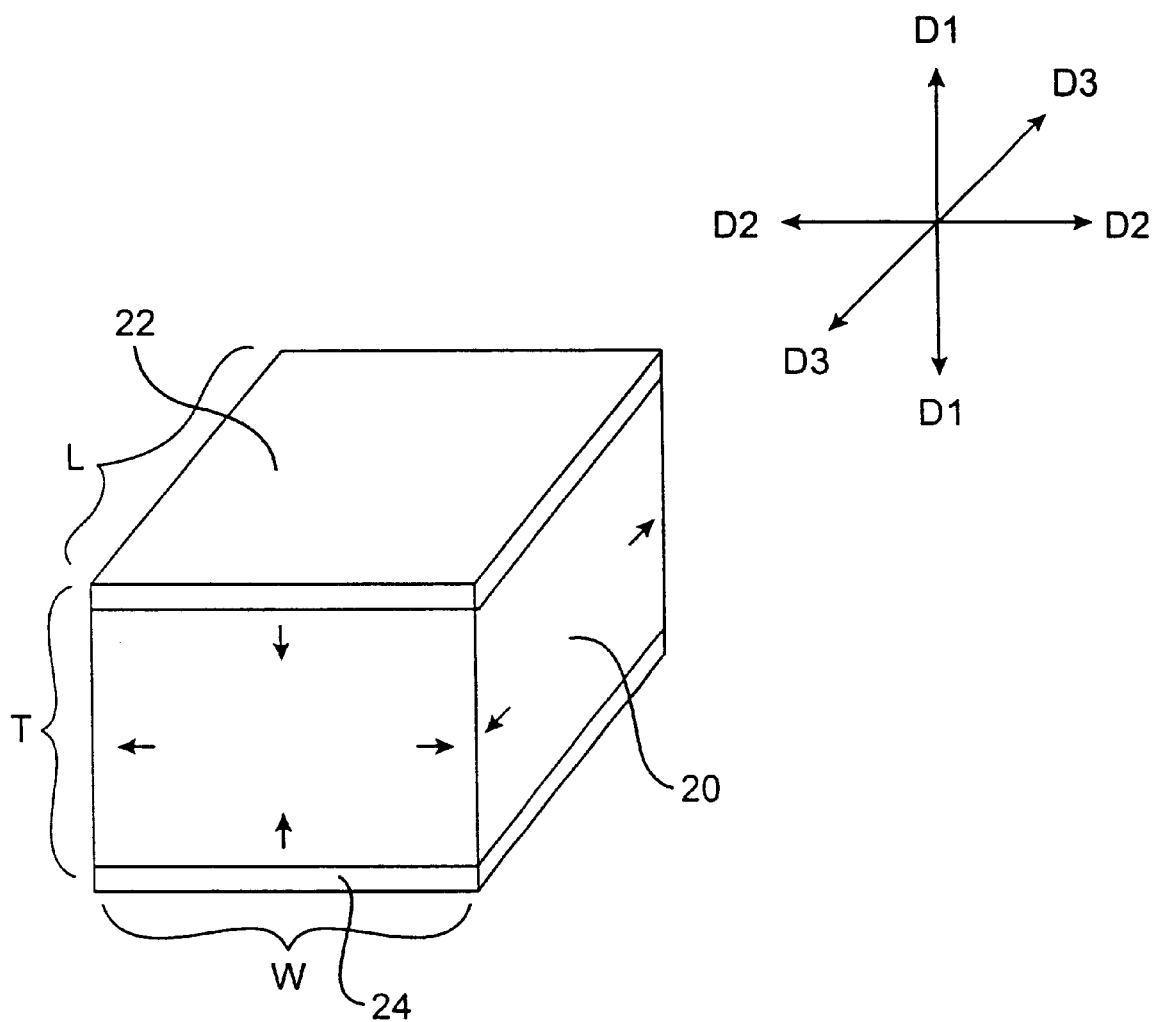
FIG. 2 is a perspective view of a single ultrasound transducer of FIG. 1.

In preferred aspects of the present invention, one or more rectangular shaped ultrasound transducers are used. FIG. 2 shows a perspective view of such a rectangular bar shaped transducer for use in conjunction with the present invention. Transducer 20 is preferably fabricated from single crystal piezoelectric materials, polycrystalline piezoelectric ceramic materials, electrostrictive or magnetostrictive materials. Transducer 20 has a width W, thickness T, and length L, as shown.

Transducer 20 has opposite electroded surfaces 22 and 24 as shown. Application of an alternating voltage to electroded surfaces 22 and 24 will cause transducer 20 to rapidly expand and contract in direction D1, thereby emitting ultrasound vibrational energy in direction D1. Such expansion and contraction in direction D1 will also cause vibrational energy to be emitted in directions D2 and D3. Specifically, as transducer 20 expands in direction D1 it will contract in directions D2 and D3, and vice versa. Accordingly, a positive thickness (T) displacement will occur simultaneously with a negative width (W) displacement and a negative length (L) displacement, and vice versa.

As is illustrated in FIG. 2, the displacement in direction D1 will be out of phase with the displacement in directions D2 and D3. Specifically, transducer 20 is shown contracting in direction D2 while expanding in directions D2 and D3. (It is to be appreciated that as transducer 20 alternatively expands in direction D1, it contracts in directions D2 and D3).

Figure 3:
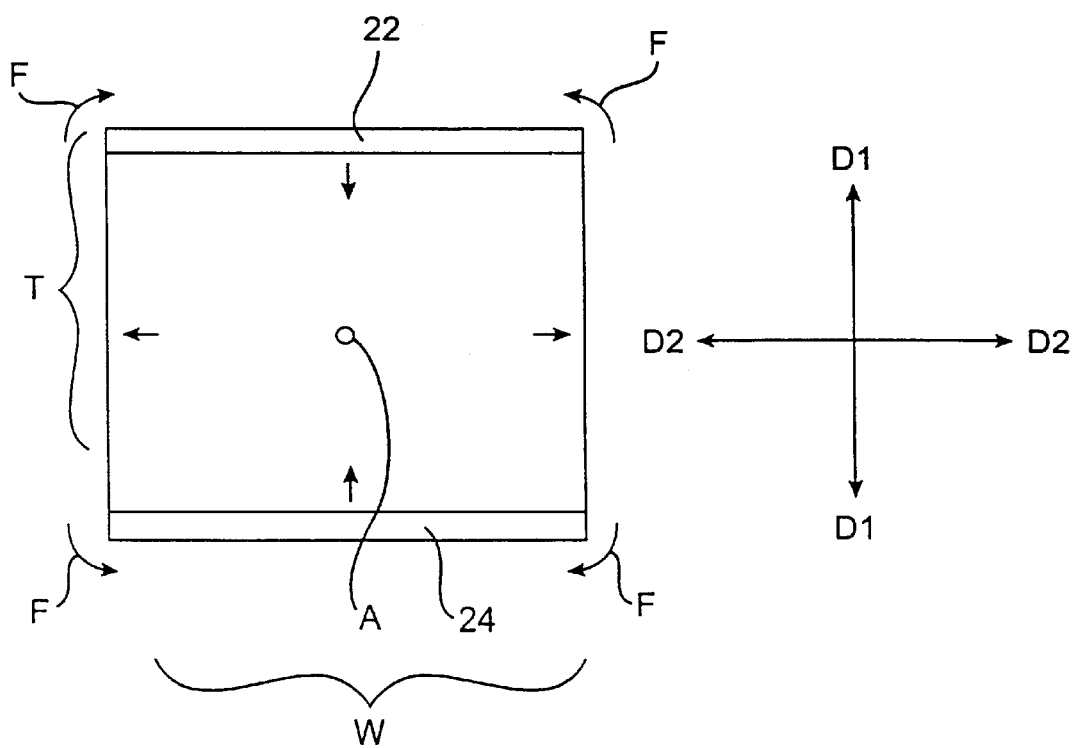
FIG. 3 is an end view of one of the transducers of FIG. 1.

Referring to FIG. 3, a beneficial aspect of such vibration is that, as the displacement in direction D1 will be out of phase with direction D2, strong but short ranged repeating transverse acoustic field flows F will be generated around the corners of the transducer. Flows F may be used to facilitate opening of pores in tissue layers.

An important advantage of transducer 20 is that it is adapted to emit vibrational energy in four radial directions, (being opposite D1 and opposite D2 directions). In contrast to phased array imaging ultrasound transducer elements, therefore, the present invention exposes more than one side to the fluid medium surrounding the catheter. In the case of a phased array element, approximately 90% of the energy is absorbed into the backing layer to assure a short impulse response in the emission from the front of the phased array element. In the present invention, no energy is absorbed by a backing layer. Rather, nearly all energy can be directed radially outwardly in directions D1 and D2 into the body lumen.

Figure 15:
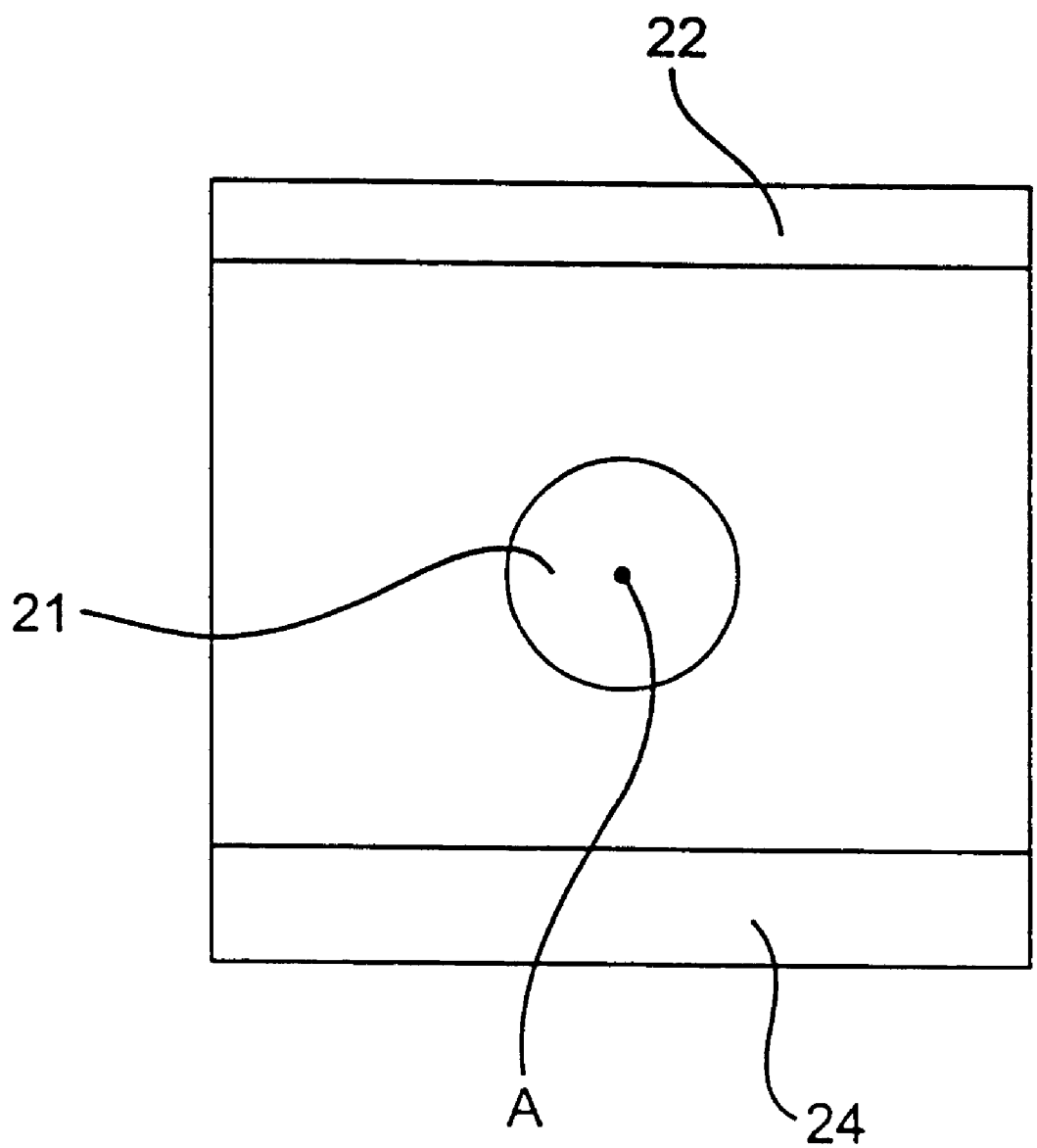
FIG. 15 is an end view of the transducer of FIGS. 1 and 2 showing a longitudinally extending hole passing therethrough.

As is shown in FIG. 15, a longitudinally extending bore 21 can be cut through transducer 20, thereby permitting access for a guidewire therethrough.

Figure 4:
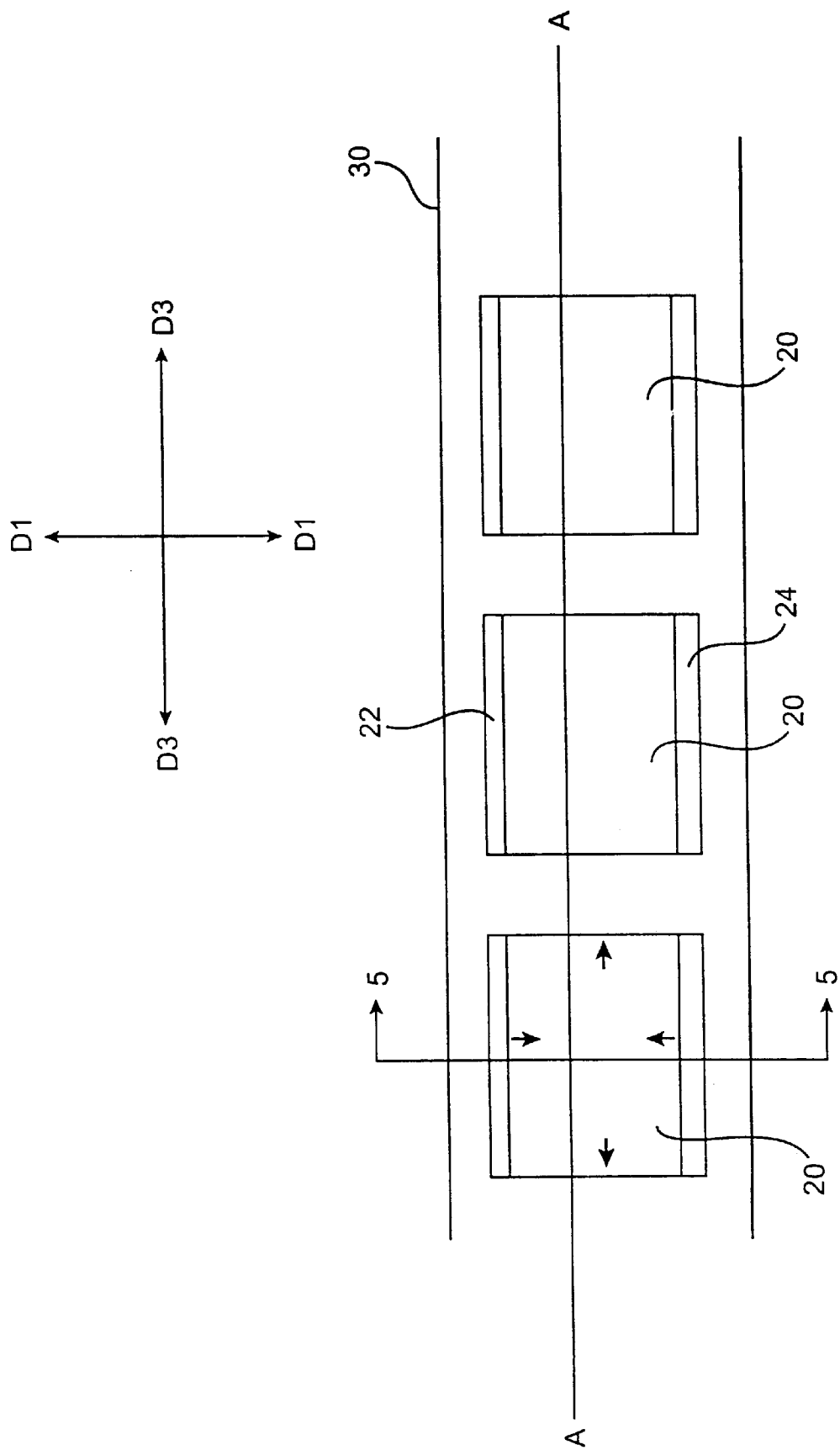
FIG. 4 is a side elevation view of the transducers of FIG. 1 in a first orientation, with their electroded surfaces parallel to the central axis of the catheter.

Emission Profiles of Rectangular Bar Shaped Transducers (A) Electroded Surfaces Disposed Parallel to the Catheter Central Axis As is shown in FIG. 4, transducers 20 may be aligned in catheter 30 with their electroded surfaces 22 and 24 parallel to axis A. As can be seen in the crosssectional acoustic RF emission profile of FIG. 5A, (wherein the distance of the radiation profile 40 from axis A corresponds to the strength of the acoustic emission), as transducer 20 contracts in direction D1, a strong negative emission profile will be generated adjacent surfaces 22 and 24. Concurrently, transducer 20 will expand in direction D2, creating a strong positive emission profile adjacent the surfaces between surfaces 22 and 24, as shown. As can also be seen, a "cloverleaf" emission profile will be generated, tending to null at approximately 45 degrees between directions D1 and D2, as shown.

Figure 5:
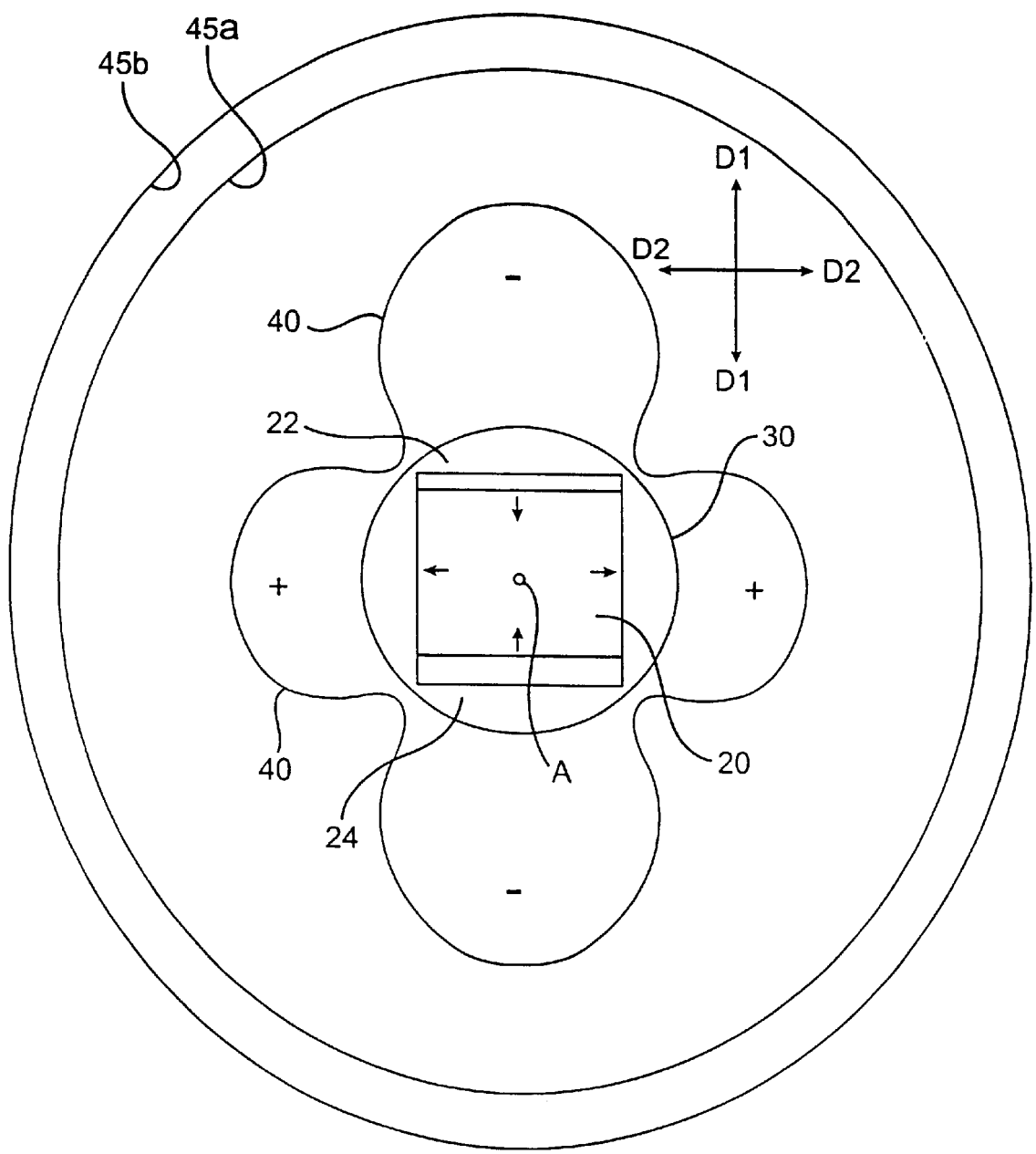
FIG. 5A is a representation of the acoustic emission pattern corresponding to FIG. 4.
FIG. 5B is a representation of pulsed operation of the ultrasound transducers, showing transducer displacement over time.

The emission profile shown in FIG. 5A is therapeutically beneficial for a number of reasons. First, it directs a high level of ultrasound energy in two perpendicular directions D1 and D2 such that by rotating catheter 30, a uniform dosage of high level ultrasound energy can be directed toward various locations on the circumference of the body lumen, as will be explained. The high level of ultrasound directed in either or both of directions D1 or D2 can be increased either by optimal dimensioning of the transducers or by the selective blockage of ultrasound emissions from two or three sides of the transducers, as will be explained.

(B) Electroded Surfaces Perpendicular to the Catheter Central Axis

Figure 6:
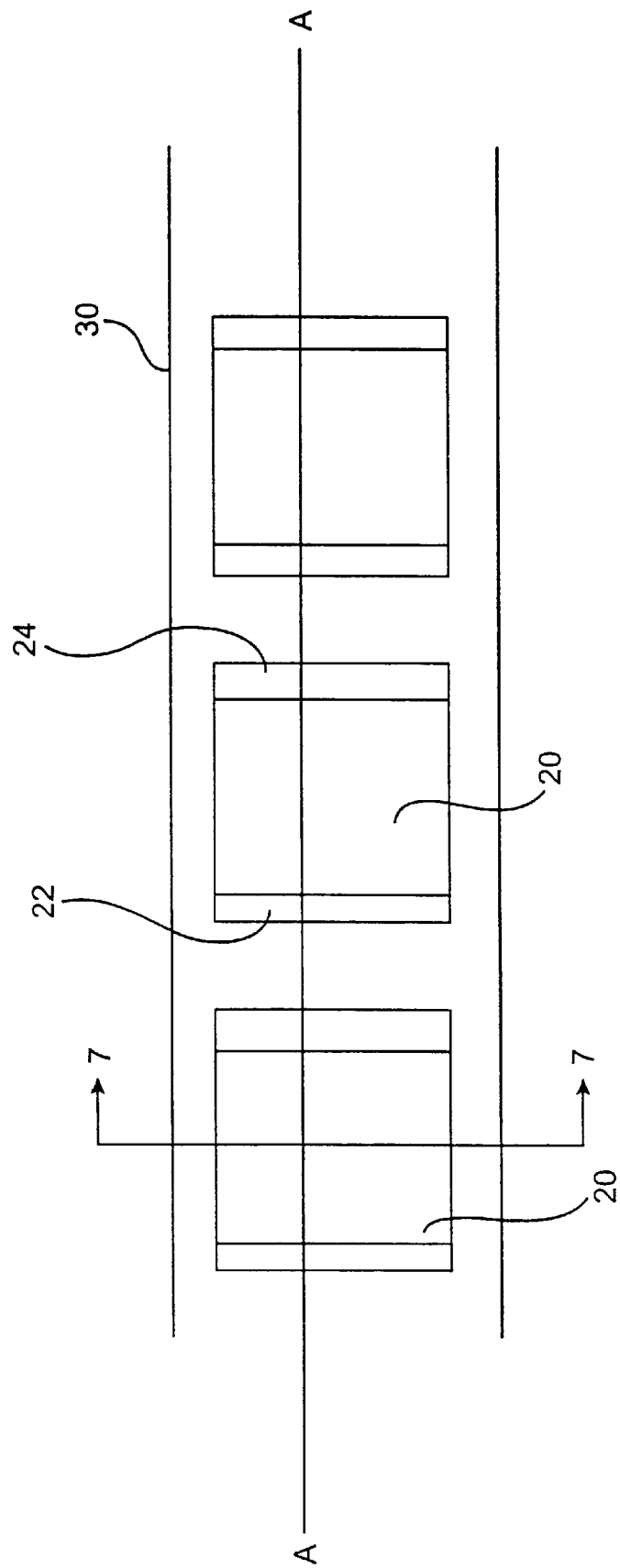
FIG. 6 is a side elevation view of the transducers of FIG. 1 in a second orientation, with their electroded surfaces perpendicular to the central axis of the catheter.
Figure 7:
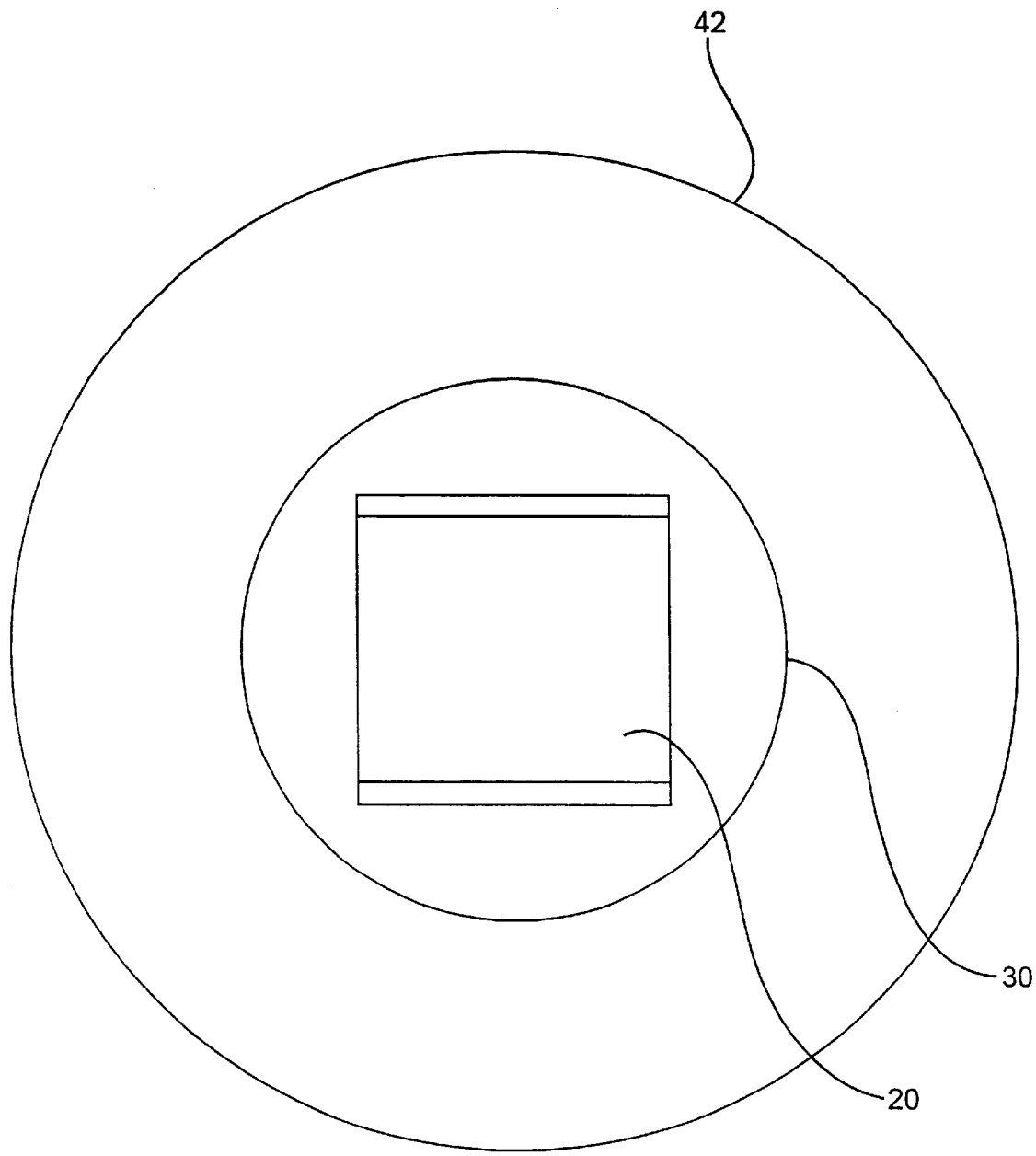
FIG. 7 is a representation of the acoustic emission pattern corresponding to FIG. 6.

FIG. 6 shows an arrangement for the positioning of transducers 20 where electroded surfaces 22 and 24 are disposed perpendicular to axis A. As is shown in FIG. 7, an acoustic emission profile 42 will tend to be circular around axis A. An advantage of this emission profile is its greater isotropic symmetry around the body of catheter 30.

Radial Compression and Longitudinal Shear Emissions

Figure 8:
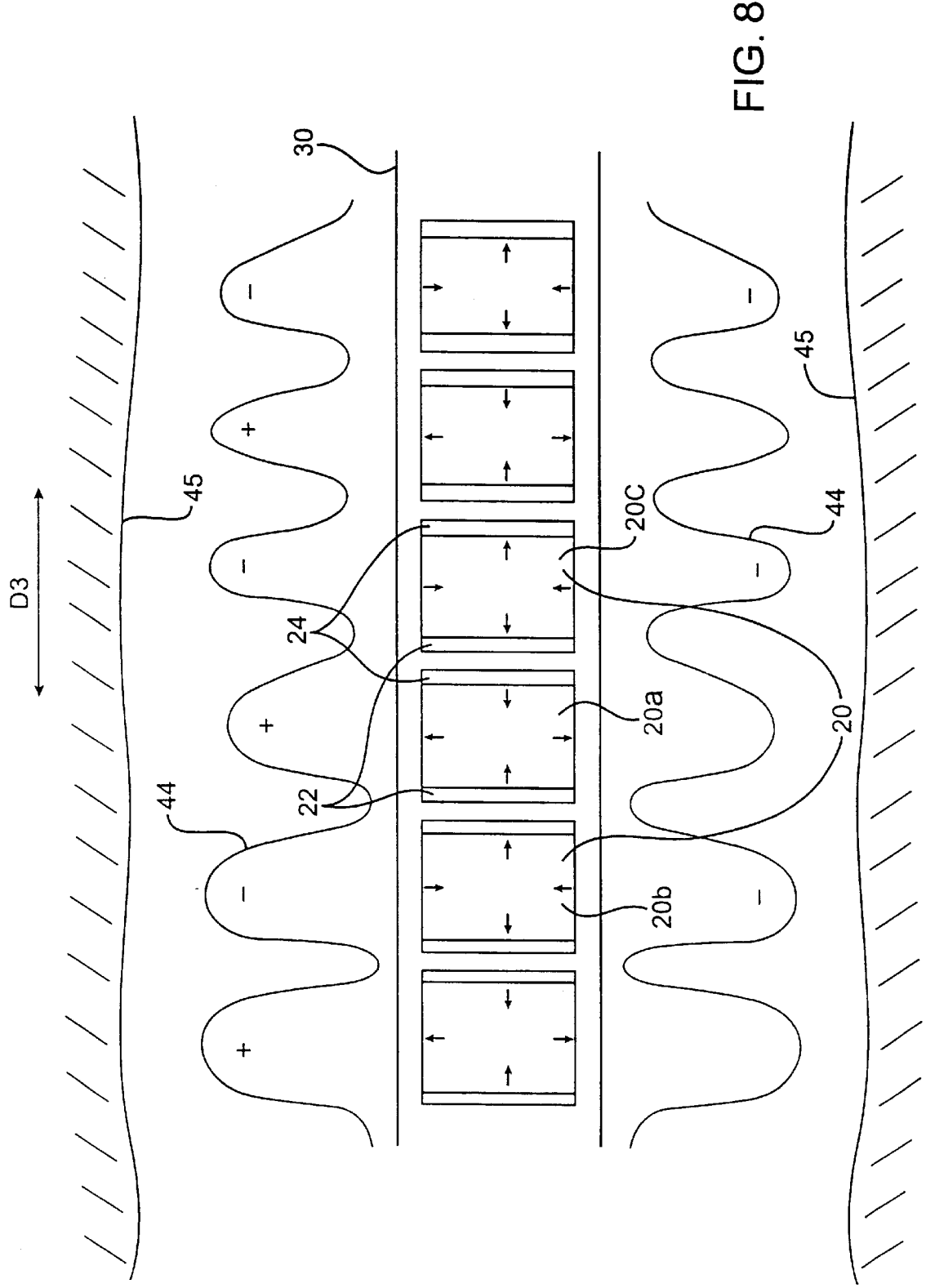
FIG. 8 is a representation of the acoustic emission pattern corresponding to FIG. 6, with successive transducers being operated 180 degrees out of phase with one another.
Figure 9:
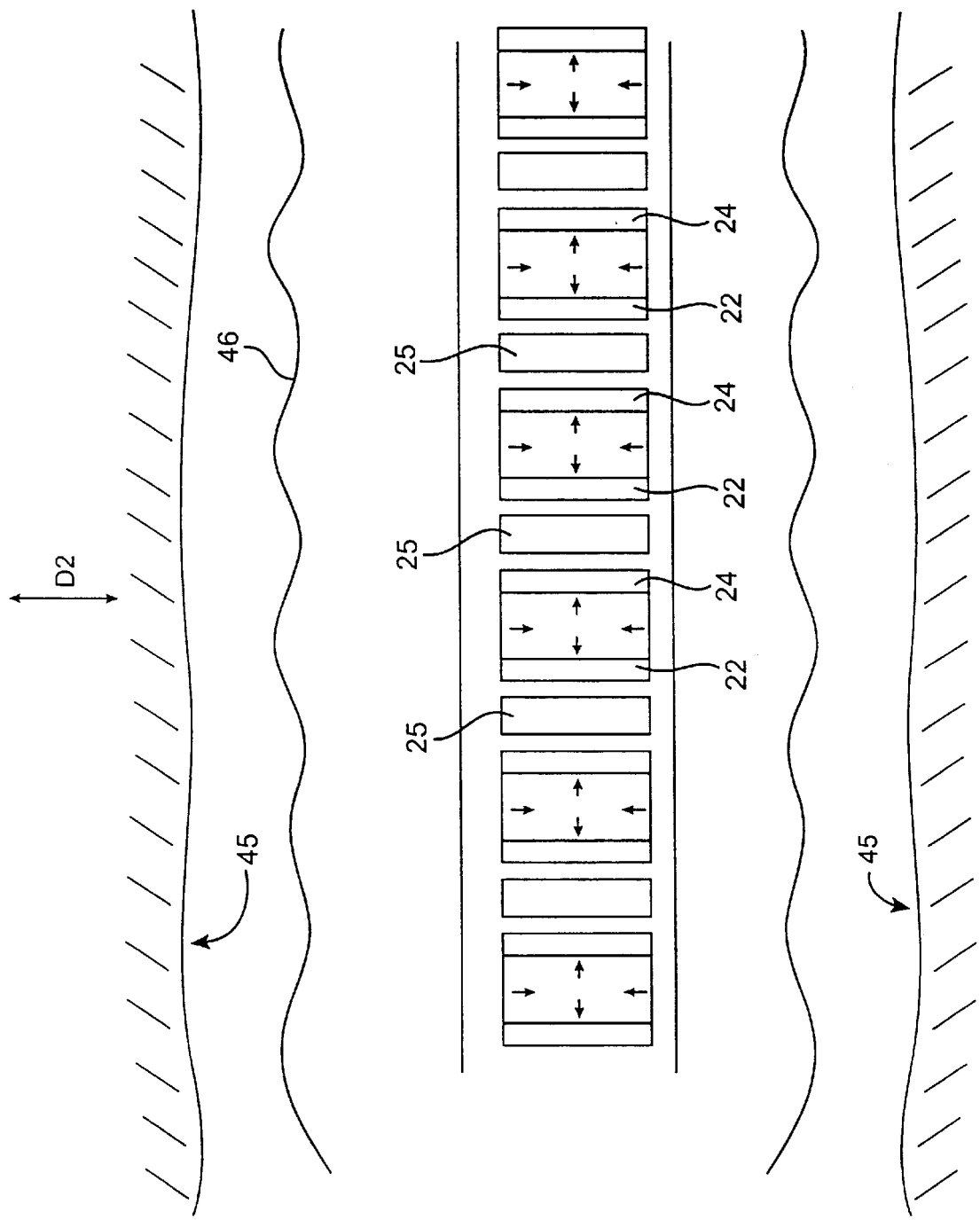
FIG. 9 is a representation of the acoustic emission pattern corresponding to FIG. 6, with successive transducers being operated in phase with one another, and with acoustic insulators disposed between adjacent transducers.

In another aspect of the present invention, either radial compression or longitudinal shear tissue displacements can selectively be generated in the walls of the body lumen. As can be seen in FIGS. 6, 8 and 9, a plurality of rectangular bar transducers 20 can be arranged with their electroded surfaces 22 and 24 positioned perpendicular to catheter axis A, as shown.

The polarities of successive transducers can be reversed such that successive transducers operate 180 degrees out of phase with one another, (as is shown in FIG. 8), to generate tissue shear displacement along lumen 45 in direction D3, as will be explained. Alternatively, successive transducers 20 can be operated in phase with their polarities disposed in the same direction, (as shown in FIG. 9), to generate longitudinal shear tissue displacement in the walls of lumen 45 in direction D2, as will be explained.

Referring first to FIG. 8, successive transducers 20 have their polarities reversed such that they operate 180 degrees out of phase with one another. Accordingly, as any transducer axially contracts, the transducers disposed on opposite sides expand. For example, as transducer 20a contracts in direction D3, transducers 20b and 20c will expand in direction D3 and vice versa. As transducer 20a contracts in axial direction D3, it will expand in radial directions D1 and D2, generating a positive radial displacement. As transducers 20b and 20c simultaneously expand in axial direction D3, they will each contract in radial directions D2 and D2, generating a negative radial displacement.

Accordingly, an acoustic emission field 44 will be generated having alternate peak positive and peak negative emissions along the length of catheter 30, as shown. Acoustic emission field 44 will thereby tend to cause shear tissue displacement along the length of the body lumen as each transducer generates peak positive and peak negative emissions alternating over time out of phase with successive transducers.

Additionally, acoustic emission field 44 is generated such that the adjacent alternating positive and negative pressure fields will cancel out at progressively greater distances from the surface of the catheter. An important advantage of this pressure field is that the canceling out of positive and negative pressures will limit the propagation distance of strong acoustic fields. Accordingly, maximal therapeutic effects will appear closer to the catheter surface, minimizing radial compression tissue displacement and increasing longitudinal tissue shear displacement.

Alternatively, as is shown in FIG. 9, should the polarity of adjacent transducers 20 be in the same direction, such that adjacent transducers operate in phase with one another, a relatively uniform acoustic emission field 46 will be generated. Specifically, respective transducers will simultaneously generate either a positive or a negative displacement in direction D2. Accordingly, a radial compression tissue displacement in direction D2 (and perpendicular direction D1), is achieved in the body lumen. Advantageously, maximum amplitude is generated with maximum dosage uniformity. In a preferred aspect of the system of FIG. 9, it may be preferable to use acoustic insulators 25 between adjacent transducers 20 so as to limit vibrational interference between the transducers in the axial (D3) direction.

Figure 12:
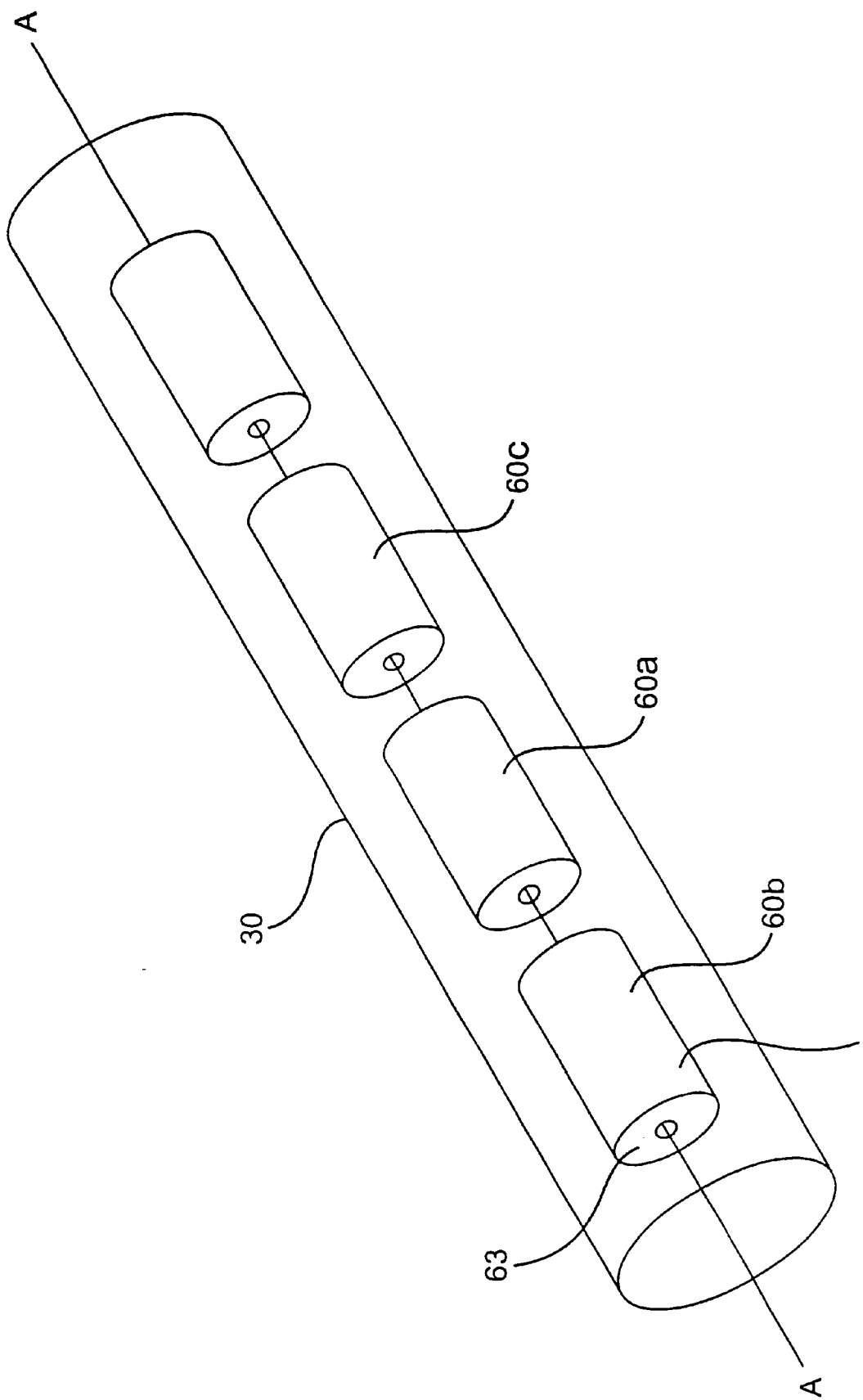
FIG. 12 is a schematic view of a plurality of cylindrical shaped isotropic ultrasound transducers disposed about the longitudinally extending central axis of a catheter.

It is to be understood that the selective generation of either radial compression (D1, D2) or longitudinal shear (D3) tissue displacements can be generated in the walls of the body lumen with transducers other than non-isotropic rectangular bar shaped transducers. For example, cylindrical or annular isotropic transducers 60, as illustrated in FIG. 12, can instead be used. When operating transducers 60 in phase, a longitudinal emission profile similar to that illustrated in FIG. 9 will be generated. When operating successive transducers 60 180 degrees out of phase with one another, a longitudinal emission profile similar to that illustrated in FIG. 8 will be generated.

Preferred Dimensions of Rectangular Bar Shaped Transducers to Achieve Resonance Vibration To achieve resonance vibration in the case of nonisotropic rectangular bar transducers, each ultrasound transducer 20 may be a cube having equal thickness (T), width (W), and length (L) dimensions. Preferably, the dimensions of such a cube shaped transducer range from a small 0.028" by 0.028" by 0.028" size through to a large 0.094" by 0.094" by 0.094" size. In an alternate preferred aspect, each non-isotropic rectangular bar ultrasound transducer 20 has a thickness (T) to width (W) to length (L) dimension ratio of 1:m:n where m=0.3 to 2, and n=0.5 to 15. Preferably, the dimensions of such a transducer 20 range from a small 0.016" by 0.016" by 0.48" size through to a large 0.094" by 0.094" by 1.63" size. In such preferred aspects, the width to thickness ratio of transducer 20 enables the transducer to operate on resonance in two perpendicular radially extending directions, thereby generating maximum displacements in the surrounding body lumen. For particular width to thickness ratios, the emission field will be stronger in a first radial direction, (typically being the D1 thickness dimension), than in a second perpendicular radial direction, (typically being the width D2 dimension). For example, when transducer 20 has a width to thickness ratio of 0.66, displacement in the thickness (T) dimension may be approximately twice the displacement in the width (W) dimension, (each displacement being 180° out of phase with the other).

An important advantage of generating emission intensity stronger in a first radial direction is that proportionally more therapeutic ultrasound energy can be directed to specific therapeutic sites of interest on the circumference of the body lumen. Uniform ultrasound dosage around and along the lumen can be achieved by translating or rotating transducer 20, as will be explained.

It is to be understood that the preferred dimensions of the present rectangular bar transducers are not limiting and that transducers of other sizes and dimension ratios may be used in the present invention.

When a plurality of axially spaced apart transducers 20 are operated, axial displacements in direction D3 will occur. By placing transducers 20 at one half wavelength increments in direction D3, they will interfere constructively Blocking Ultrasound Emissions from Multiple Sides of Rectangular Bar Shaped Transducers In a preferred aspect of the present invention, rectangular bar shaped transducers 20 have at least one side disposed parallel to the central axis of the catheter acoustically insulated to block the emission of ultrasound energy therefrom. As such, ultrasound energy can only be released from the unblocked sides of the transducer, raising the intensity level of the ultrasound delivered to the wall of the lumen, by directing the ultrasound energy in a preferred radial direction, or directions.

Figure 10:
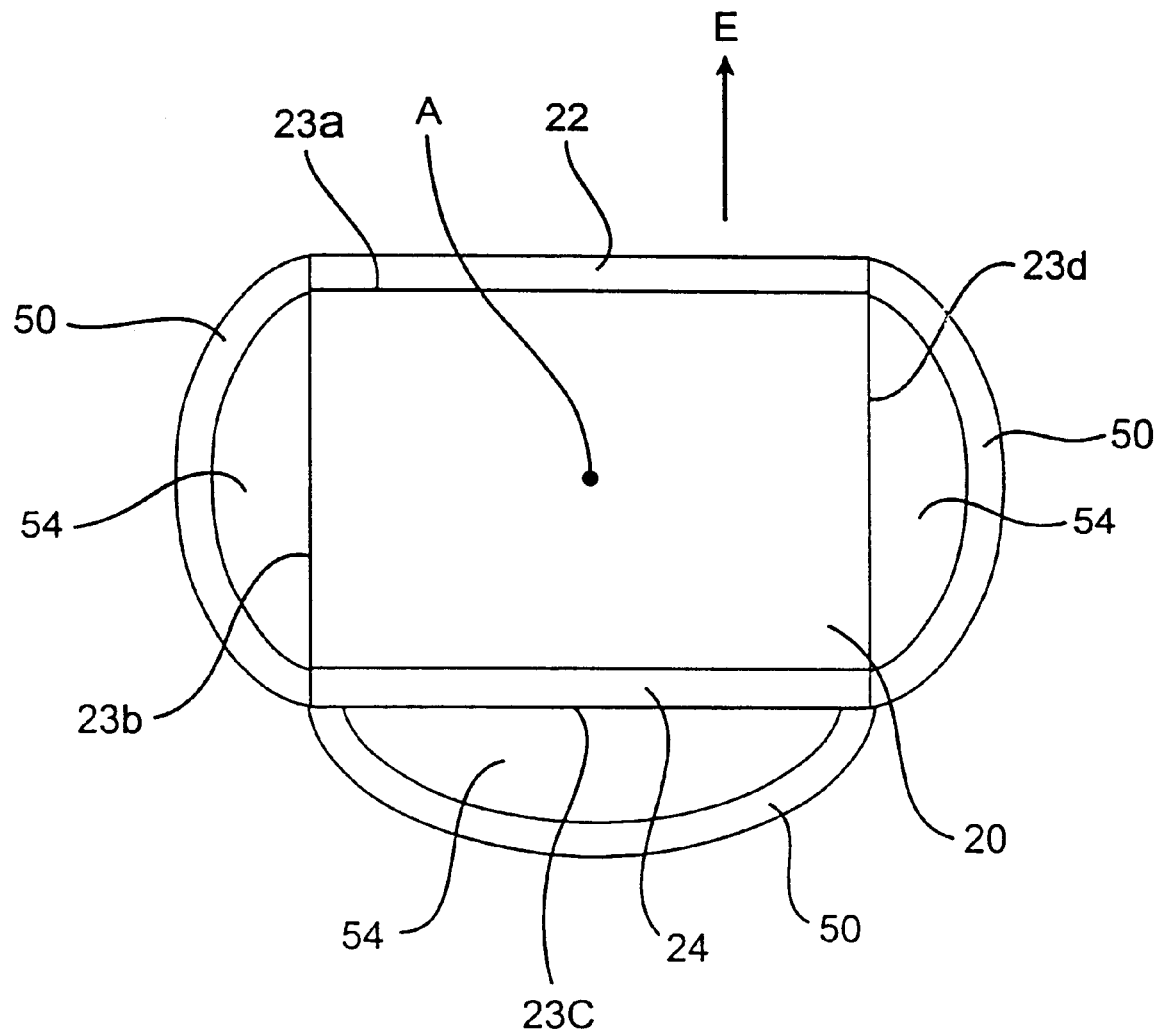
FIG. 10 is an end view of a rectangular bar shaped ultrasonic transducer, having three surfaces acoustically insulated by air cavities.

Referring to FIG. 10, transducer 20 can optionally have surfaces 23b, 23c and 23d encompassed by an air cavity 54 and a structural member 50. The presence of air cavity 54 between structural member 50 and surfaces 23b, 23c and 23d of transducer 20 will substantially inhibit ultrasound emission therefrom. Accordingly, the acoustic energy of transducer 20 will instead be emitted from surface 23a in the direction shown by arrow E.

Structural member 50 may be made of a polycarbonate or liquid crystal polymer and be surrounded by a catheter skin made of polyethelene, PET or PTFE, heat shrunk around transducers 20 and structural member 50.

Figure 11:
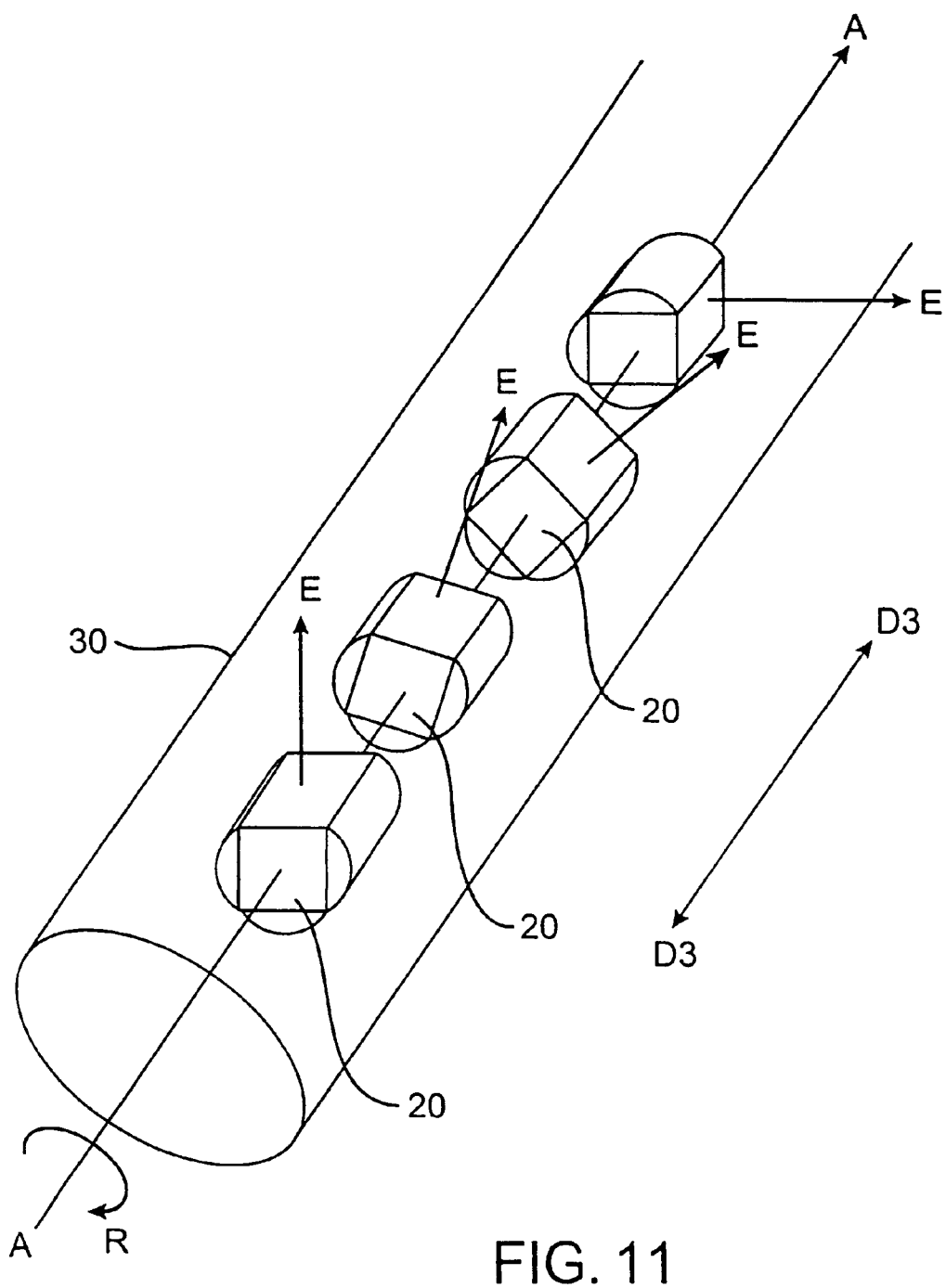
FIG. 11 is a schematic representation of a plurality of rectangular bar shaped ultrasound transducers disposed along the longitudinally extending central axis of a catheter, with successive transducers being rotated with respect to the central longitudinal axis of the catheter, showing ultrasound energy emitted in different radial directions along the length of the catheter.

Referring to FIG. 11, a plurality of successive transducers 20, each having their surfaces 23b, 23c and 23d acoustically insulated, can be positioned such that surfaces 23a are rotated with respect to one another about axis A, as shown. Successive arrows E show the direction in which ultrasound energy is directed for each of successive transducers 20.

By rotating catheter 30 about axis A in the direction shown by arrow R, or alternately, by translating catheter 30 in direction D3, a uniform dose of ultrasound energy can be sequentially directed to the walls of the body lumen, as will be explained herein.

Ultrasonic Catheter Systems Comprising Cylindrical Shaped Transducers

Figure 14:
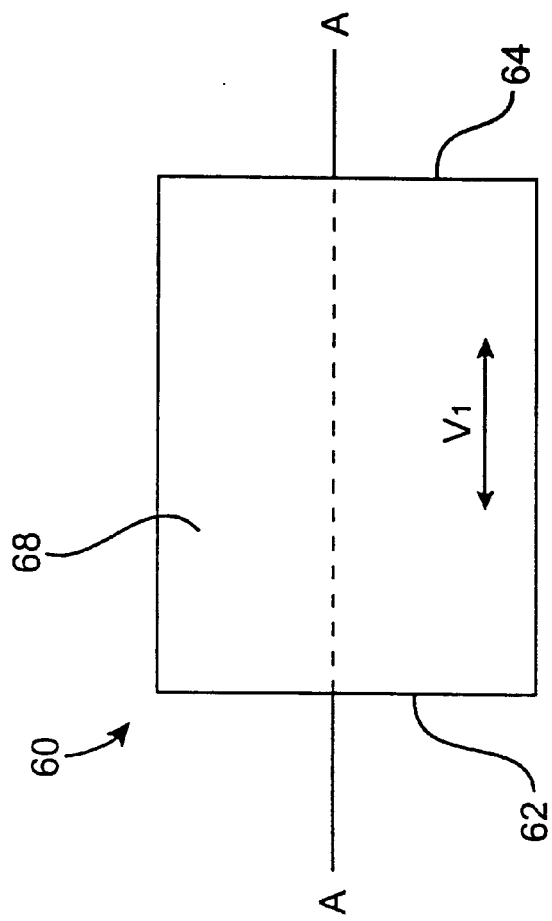
FIG. 14 is an side view of a cylindrical shaped transducer of FIG. 12.
Figure 13:
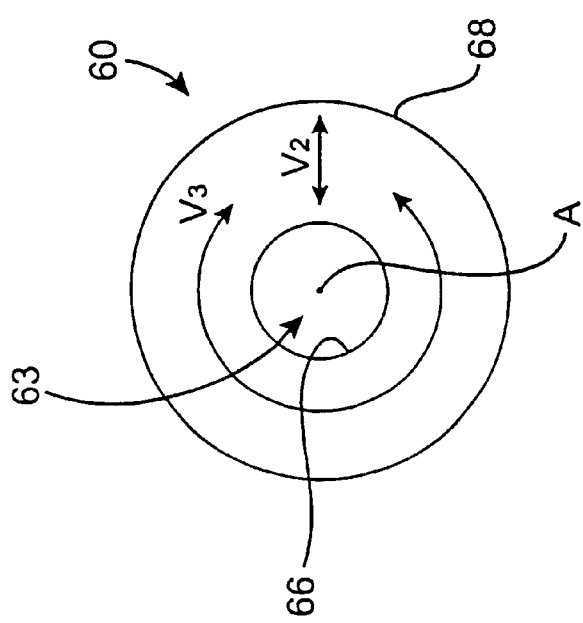
FIG. 13 is an end view of a cylindrical shaped transducer of FIG. 12.

FIG. 12 schematically shows a catheter system with a plurality of cylindrical shaped transducers 60 disposed parallel, (and preferably generally collinear), with catheter central axis A. FIG. 13 shows an end view and FIG. 14 shows a side view of an exemplary transducer 60.

Being symmetric about axis A, each transducer 60 will emit an isotropic acoustic field radially outwardly from catheter 30.

In preferred aspects, each transducer 60 has a longitudinally extending bore 63 passing through defining an inner surface 66. Bore 63 passing through transducer 60 can provide a opening for receiving a guidewire passing therethrough.

In a first aspect, flat ends 62 and 64 which are disposed perpendicular to axis A serve as the electroded surfaces. In a second aspect, inner surface 66 and outer surface 68 serve as the electroded surfaces. When surfaces 66 and 68 serve as the electroded surfaces, an inner flexible metallic tube may be received through bore 63, contacting electrode surface 66 and an outer flexible metallic tube may be used to provide contact with the exterior electroded surface 68.

When either surfaces 62 and 64 or 66 and 68 serve as the electroded surfaces, the acoustic emission profile will tend to be isotropic about the central axis of the catheter.

A lower frequency resonance (in the length mode, shown as V1 in FIG. 14) is achieved when ends 62 and 64 serve as the electroded surfaces, allowing greater penetration of ultrasound energy. The thickness and cylindrical resonances may also be excited (as explained below). Conversely, when inner and outer curved surfaces 66 and 68 serve as the electroded surfaces, a higher frequency resonance (in the wall thickness mode, shown as V2 in FIG. 13) is achieved.

The transducer may also be operated in the lower frequency (cylindrical mode, shown as V3 in FIG. 13 and length mode as shown as V1 in FIG. 14) with inner and outer curved surfaces 66 and 68 serving as the electroded surfaces.

When successive transducers 60a, 60b and 60c are operated 180 degrees out of phase with one another, (with either surfaces 62 and 64 or 66 and 68 serving as the electroded surfaces), an emission profile similar to that of FIG. 8 will be generated, causing axial shear tissue displacement. Conversely, when successive transducers 60a, 60b and 60c are operated in phase with one another, (with either surfaces 62 and 64 or 66 and 68 serving as the electroded surfaces), an emission profile similar to that of FIGS. 9 will be produced.

Preferred Dimensions of Cylindrical Transducers

Cylindrical transducers preferably have dimensions which range from a small 0.04011 diameter and a small 0.0611 length though to a large 0.133" diameter and a 1.775" length. It is to be understood that the preferred dimensions of the present cylindrical shaped transducers are not limiting and that transducers of other sizes and dimension ratios may be used in the present invention. Transducer wall thickness may be as small as 0.007", limited only by required mechanical integrity of the device.

When a plurality of axially spaced apart transducers 60 are operated, axial displacements in direction D3 will occur. By placing transducers 60 at one half wavelength increments in direction D3, they will interfere constructively.

Wiring of Transducers

Transducers 20 or 60 may be wired in parallel, necessitating only two leads passing through the catheter. However, independently wiring the various transducer electrodes can accomplish effects such as staggering the emissions of transducers so as to promote a pumping action along the surface of the catheter. Moreover, by mixing frequencies (from different size transducers), waves based on the summation of variable frequency components and constructive interference, which exhibit exceptionally large displacements can be generated.

Wrapped Copolymer Ultrasound Transducer

The present invention provides a system for delivering therapeutic ultrasound energy comprising a thin film polymer or copolymer transducer wrapped around a portion of the length of a catheter.

Figure 16:
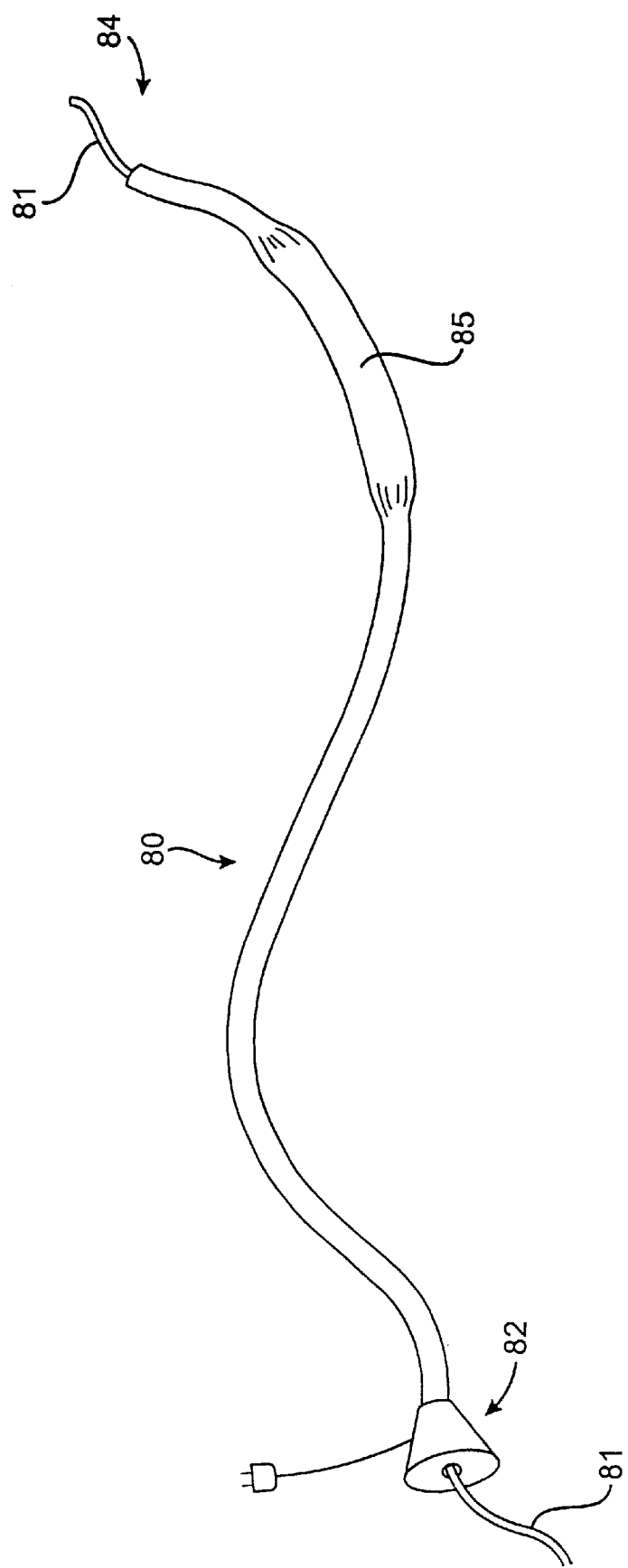
FIG. 16 is a perspective view of a catheter system comprising a flexible copolymer ultrasound transducer wrapped around a portion of its length.

Referring to FIG. 16, a catheter 80, having a proximal end 82 and a distal end 84 with a guide wire 81 passing therethrough is provided. Transducer 85 preferably comprises a thin polymer or copolymer film wrapped around a portion of the length of catheter 80 as shown. A component of the thin polymer film transducer preferably comprises polyurethane and of the thin copolymer film transducer preferably comprises PVDF.

Copolymer transducer 85 may comprise P(VDF-TrFE) irradiated with 40 to 100 Mrad of 3 MeV electrons. Such a material has a piezoelectric displacement on the order of 4%. Such copolymers are typically provided as sheets having thicknesses in the range from 25 to 40 microns, with sputtered electrodes on opposite faces.

The transverse and longitudinal strains can be tuned over a large range by both variations in the electron radiation dosage and by processing temperature, and by physically stretching the copolymer. When the copolymer is stretched, the transverse strain parallel to the direction of the stretch (and parallel to the polymer chains) can be as large or larger than the longitudinal (perpendicular to the electrodes) strain. When the copolymer is not stretched, the ratio of the transverse strain with respect to the longitudinal strain can be as low as −0.2.

In one aspect of the present invention, transducer 85 is configured to emit in the longitudinal mode. By not stretching the copolymer, transverse strain is suppressed. For a $d_{33}$ of −350 Pico meters/volt, one layer of copolymer at 25 microns thick subjected to 100 volts will generate a longitudinal strain of 0.35 microns. A 5.5 French catheter with a 0.018 inch guidewire lumen would support approximately 20 layers of the copolymer. Such a system might show a displacement of 1.9 microns, supporting drive levels in excess of 150kV per centimeter.

In another aspect, transducer 85 is configured to take advantage of the strong transverse mode brought on by stretching the copolymer. In this aspect, the copolymer is wrapped around the catheter with the direction of polymer chains (direction of stretching) parallel to the circumference. The stretched copolymer may have equal magnitude (but opposite signed) $d_{31}$ and $d_{33}$ values, typically being 275 Pico meters/volt. Anticipated device amplitude is 14 microns for a 1000 volt drive.

Advantageously, operation of transducer 85 generates a uniform radial ultrasound emission both around the circumference and along the length of transducer 85. Accordingly, it is not necessary either to rotate or to axially translate catheter 80 to deliver a uniform dose of ultrasound energy along a portion of the length of the body lumen.

Figure 17:
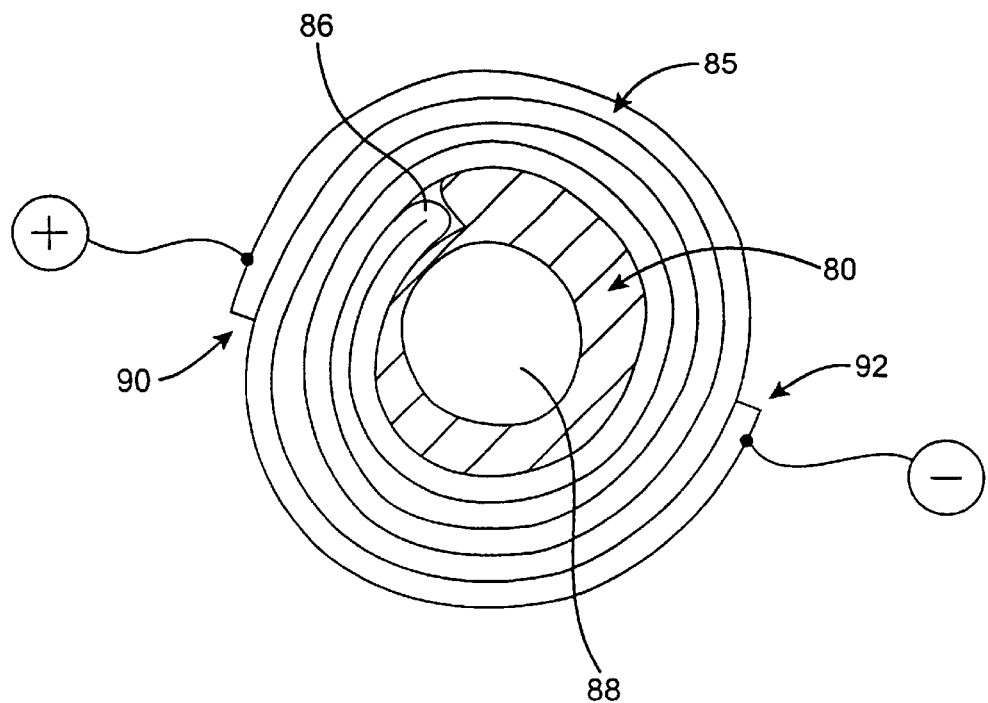
FIG. 17 is a sectional view of the transducer and catheter system of FIG. 16.
Figure 18:
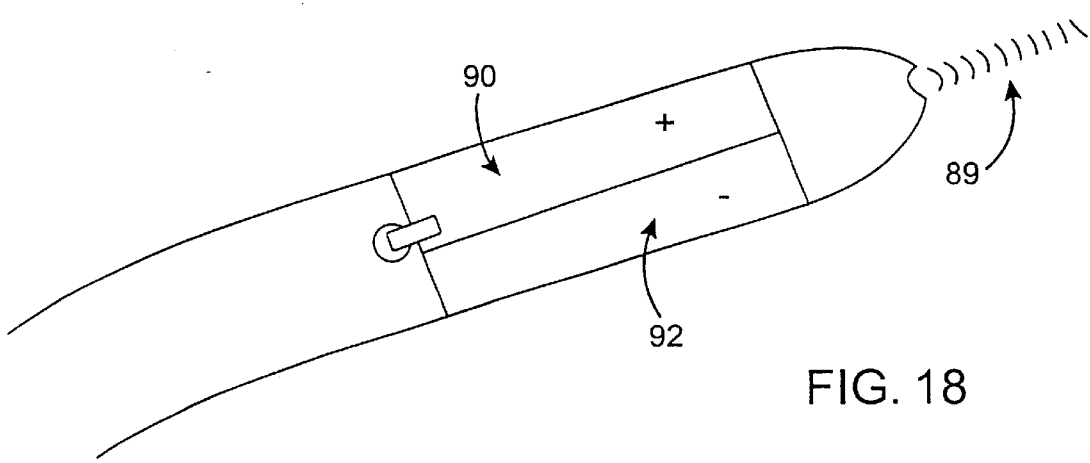
FIG. 18 is a side elevation view of the distal end of the transducer and catheter system of FIG. 16.

Referring to FIG. 17, copolymer transducer 85 can be bent over upon itself at location 86 and then wrapped around the body of catheter 80, as shown. A guide wire lumen 88 having a guidewire 89 (FIG. 18) is also provided. By folding transducer 85 over upon itself prior to its being wrapped around catheter 80, positive end 90 and negative end 92 are disposed at an outer surface of the catheter system for attachment to respective positive and negative electrode leads.

Figure 19:
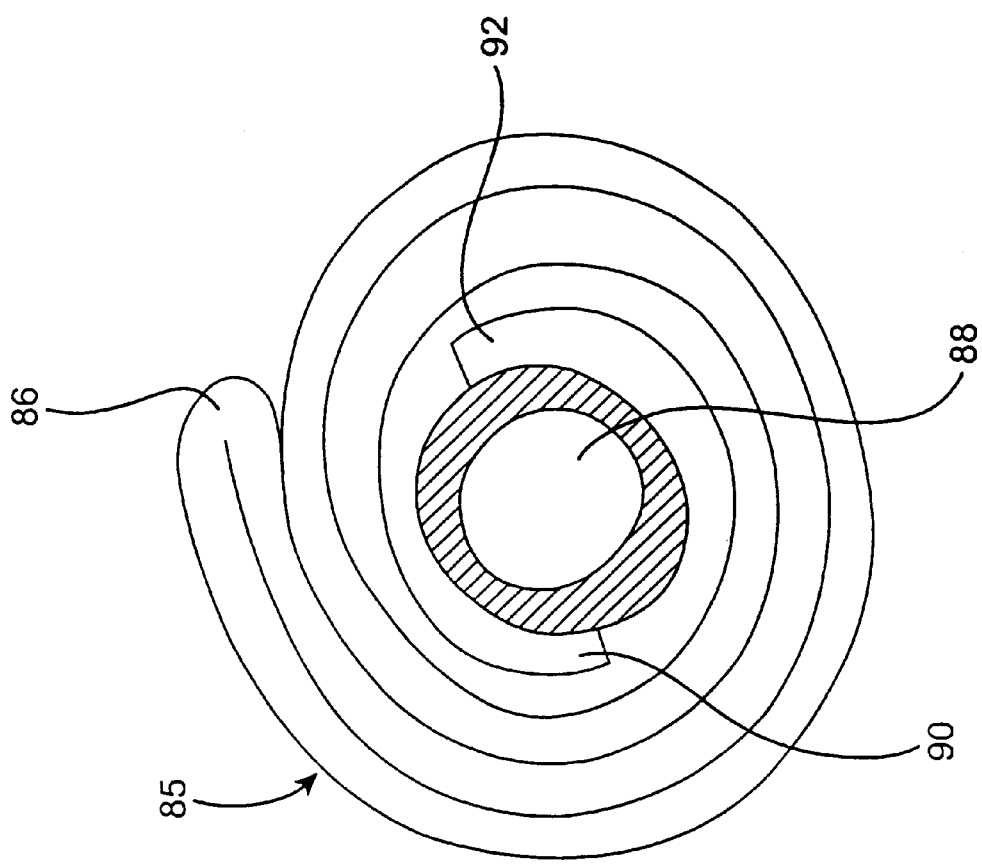
FIG. 19 is a perspective view of a catheter system comprising a flexible copolymer ultrasound transducer wrapped in an alternate fashion around a portion of its length.

Alternatively, as seen in FIG. 19, both the positive and negative ends 90 and 92 of transducer 85 can be covered by the transducer itself, providing a smooth exterior surface.

Comprising a very thin film, an important advantage of transducer 85 is that it can be constructed to be sufficiently small in diameter (for example, less than 5.5 French), such that it can be passed within a stented region of a body lumen. Having a small diameter, and being flexible, transducer 85 can be passed through narrow tortuous lumen paths.

Balloon Systems for Therapeutic Agent Delivery and Evacuation

The present invention comprises a number of different balloon systems which can each be used with any of the preferred ultrasound transducers, or transducer arrangements as set forth herein. For illustration purposes, the present balloon systems are shown as surrounding a plurality of axially spaced apart ultrasound transducers. It is to be understood that the present balloon systems may be used with the present non-isotropic rectangular bar shaped transducers, the present isotropic cylindrically shaped transducers, the present thin wrapped polymer or copolymer transducer, or any other therapeutic ultrasound transducer system which may comprise one or more than one transducer.

In the present invention, balloon systems are provided for isolating a therapeutic agent in the section of the body lumen which is exposed to ultrasound energy from the transducers. Systems for removing excess or unused therapeutic agent after treatment are also included.

An important advantage of all of the present ballooning systems is their local delivery of therapeutic agents which may include engineered genes and other antiproliferative compounds to particular sites of interests in a body lumen. The present systems provide optimal means of controlled drug delivery to body lumens in conjunction with delivery of ultrasound energy there along, thereby increasing the efficiency and safety of drug and therapeutic agent delivery. An additional important advantage of the applicant's balloon systems is their capacity for retrieval of unused therapeutic agents from the body lumen. Retrieval of such unused therapeutic agents decreases the risk of unwanted systemic side effects.

Specifically, the present balloon systems operate by providing an obstruction to blood flow in conjunction with protective and controlled release of the drug to the site of interest, as set forth in the following exemplary systems.

Figure 20:
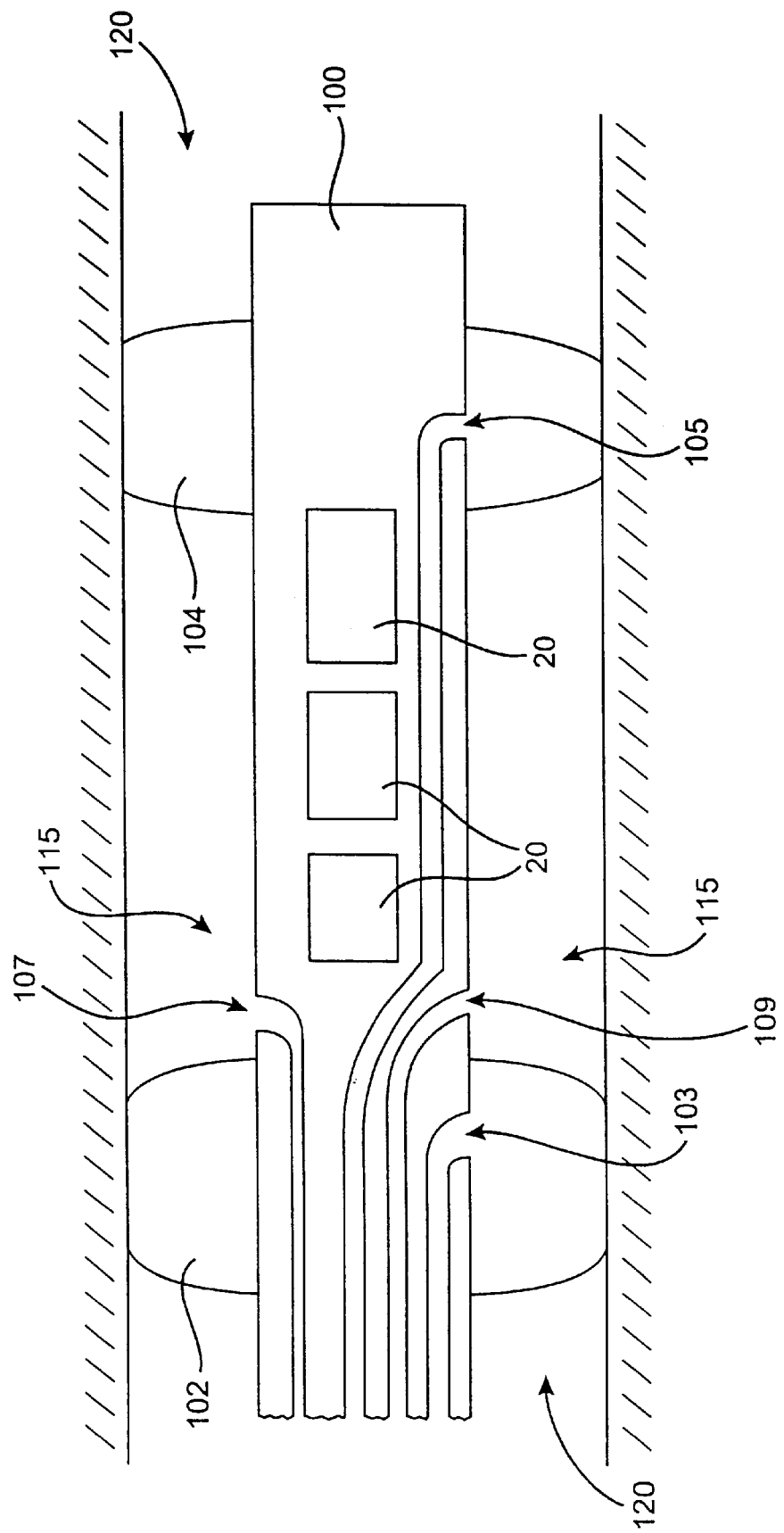
FIG. 20 is a schematic sectional view of a double balloon system for infusing therapeutic agents into a body lumen used in conjunction with the present ultrasound transducers.

In a first balloon system, shown in FIG. 20, catheter 100 is provided with a proximal balloon 102 and a distal balloon 104. Proximal balloon 102 is preferably inflated through proximal balloon inflation port/lumen 103 and distal balloon 104 is preferably inflated by distal balloon inflation port/lumen 105. Catheter 100 supports ultrasound transducers 20 (shown here as 3 transducers, but understood to encompass varying numbers of transducers including a single transducer), which are preferably disposed between proximal balloon 102 and distal balloon 104.

After catheter 100 is received in lumen 120, the proximal and distal balloons 102 and 104 are inflated, thereby providing a fluidly sealed region 115 therebetween. Concurrently with the operation of ultrasound transducers 20, a therapeutic agent can be pumped through infusion port 107, thus entering region 115. A flushing port 109 can be used to withdraw the excess therapeutic agent upon the completion of the treatment before the proximal and distal balloons 102 and 104 are deflated and catheter 100 is removed from lumen 120.

Figure 21:
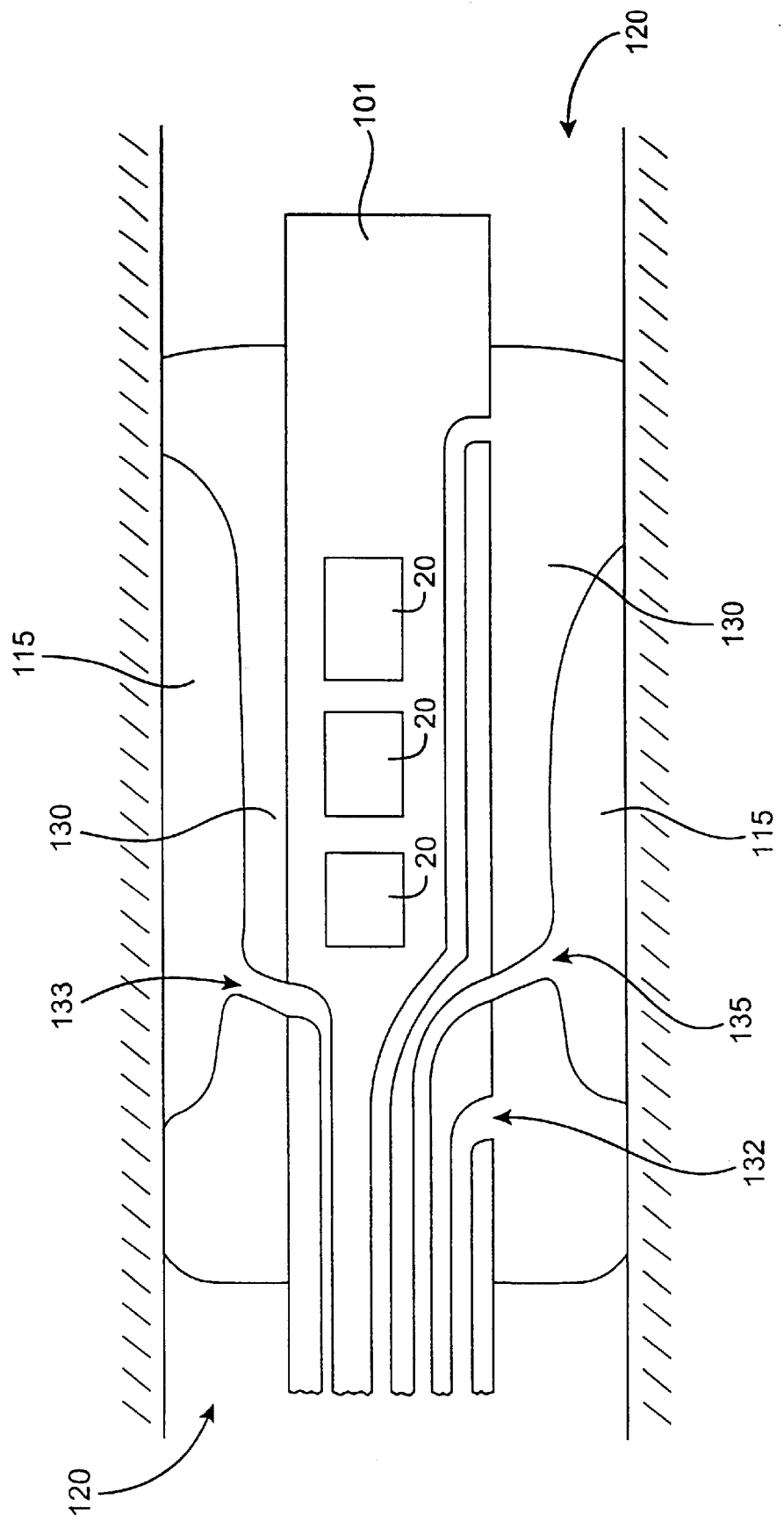
FIG. 21 is a sectional representation of a dog bone shaped balloon system for infusing therapeutic agents into a body lumen used in conjunction with the present ultrasound transducers.

In a second balloon system, shown in FIG. 21, catheter 101 may comprise a dog bone shaped balloon 130 which, when inflated after catheter 101 is received in lumen 120, operates to seal a region 115 for treatment by a therapeutic agent. Dog bone shaped balloon 130 is inflated by port 132. Therapeutic agent infusion port 133 and evacuation port 135 operate similar to that of ports 107 and 109, of FIG. 21, respectively.

Figure 22:
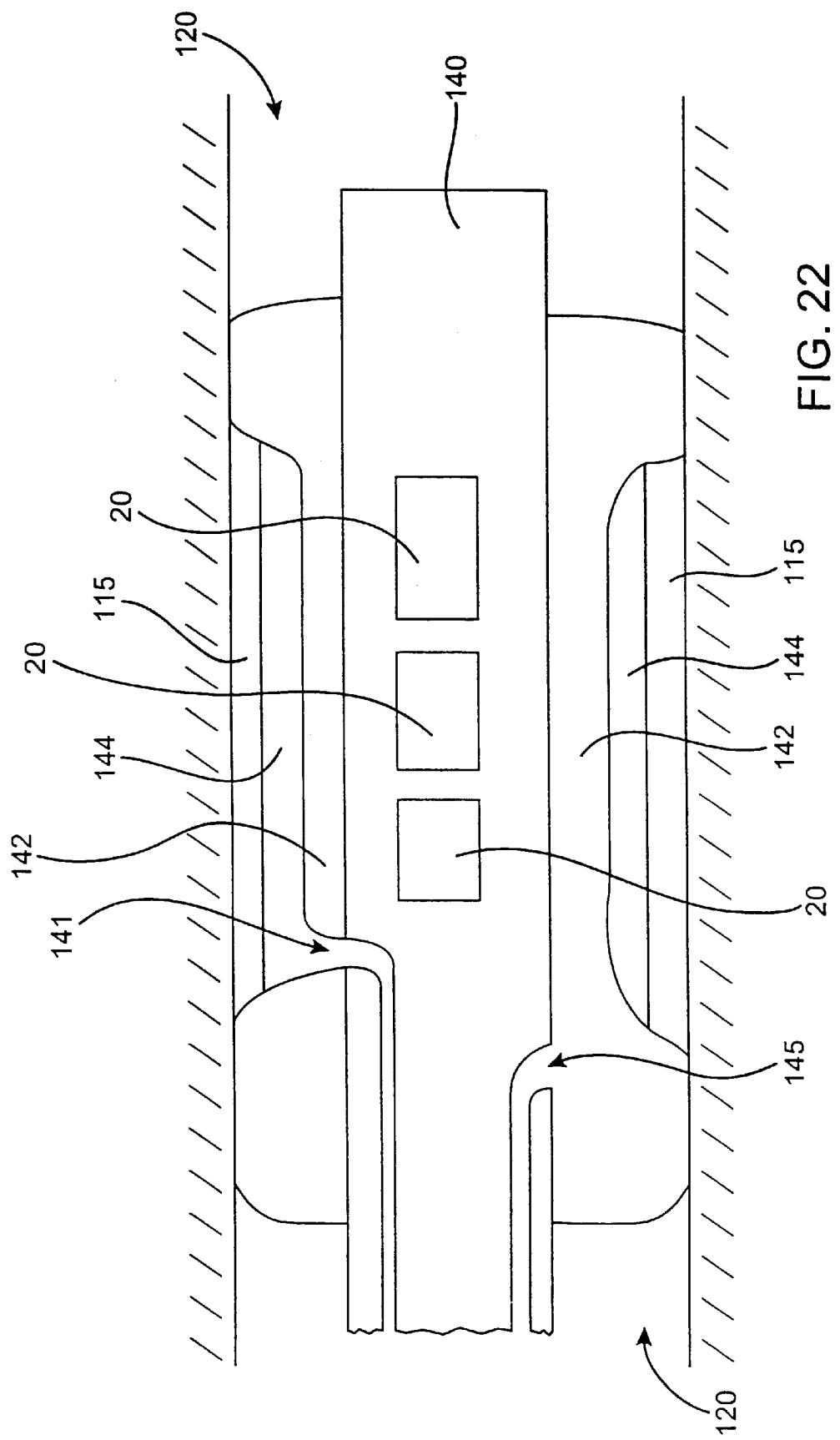
FIG. 22 is a sectional representation of a dog bone shaped balloon having a second porous balloon disposed thereover for infusing therapeutic agents into a body lumen used in conjunction with the present ultrasound transducers.

In a third balloon system, shown in FIG. 22, catheter 140 comprises a first dog-bone shaped balloon 142 surrounded by a second balloon 144 covering the central portion of balloon 142. Therapeutic agents enter balloon 144 through infusion port 141. Balloon 142 is inflated by port 145. Balloon 144 is porous such that, when inflated, therapeutic agents will pass therethrough into region 115 and thus be absorbed into body lumen 120.

Figure 23:
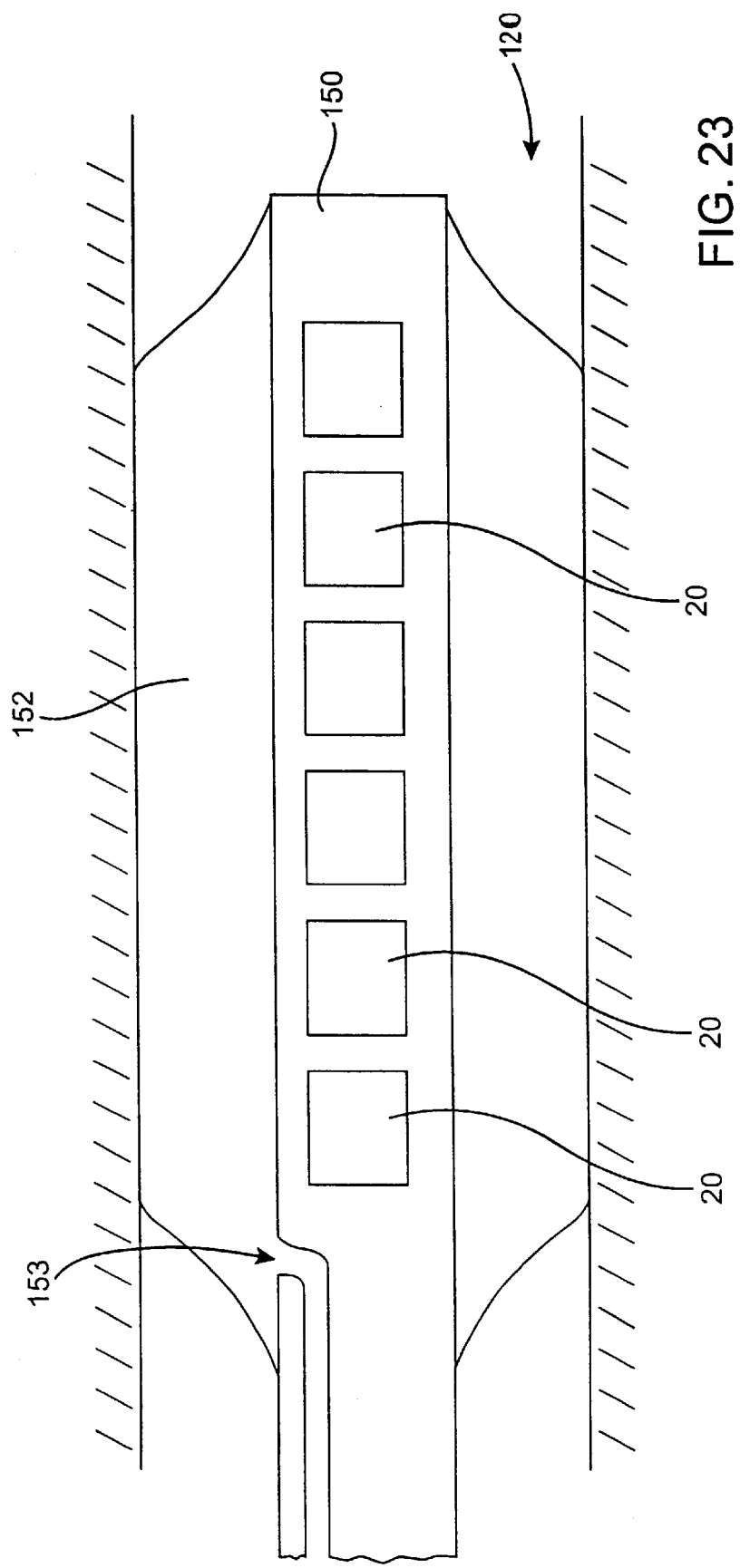
FIG. 23 is a sectional view of a porous balloon system for infusing therapeutic agents into a body lumen used in conjunction with the present ultrasound transducers.

Another advantage of the balloon systems of FIGS. 21, 22 and 23 is that blood can be removed from area 115 prior to the therapeutic agent being delivered thus preventing the blood from acting as a dilutant or inhibitor. At the conclusion of the drug therapy, any unused drug can be removed by aspirating it out. An advantage of the balloon system shown in FIG. 22 is that a minimum amount of expensive drug can be used as the drug or other therapeutic agent is not used to inflate the dog bone shaped balloon. Rather, a separate liquid such a saline can be used for inflation of balloon 142.

In a fourth balloon system, shown in FIG. 23, catheter 150 comprises a single porous balloon 152 extending over the length of transducers 20. Balloon 152 is inflated with therapeutic agent by way of infusion port 153. In the instance where balloon 152 is compliant, when fully inflated, balloon 152 will inflate to fit a large range of lumen sizes, anchoring against body lumen 120 and, being porous when inflated, will pass therapeutic agent therethrough directly into the walls of the body lumen. In the instance where balloon 152 is instead non-compliant, (and thus inflates only to a fixed size), the size of the pores in the balloon will remain constant and will regulate the flow of the liquid therapeutic agent.

Providing a Uniform Dosage of Ultrasound Energy To A Body Lumen

An important aspect of the present invention is the ability to provide a uniform dosage of ultrasound energy along a target treatment length of a body lumen. As defined herein, a uniform dosage of ultrasound energy corresponds to ultrasound energy producing a uniform biological effect around the circumference of the body lumen. In a preferred aspect, the biological effect is the reduction of neointimal hyperplasia.

In a preferred aspect of the invention, the uniform dosage of ultrasonic energy received at any one point along the length of the lumen varies by no more +6 decibels. Also in a preferred aspect of the invention, the uniform dosage of ultrasonic energy will be applied over a length greater than the diameter of the lumen being treated, typically being at least 0.8 cm (with more preferred lengths set forth above).

The present uniform dosage of ultrasound energy corresponds to a uniform biological effect around the circumference of the body lumen which can be achieved by a variety of different acoustic bio-effects, as generated by the present therapeutic ultrasound catheter systems.

For example, the uniform dosage can be achieved by mechanical bio-effects related to cavitation, wherein the amplitude of the peak acoustic pressure is preferably greater than the threshold for cavitation to occur, and wherein the magnitude of the effect would increase with amplitude beyond this threshold. The magnitude of the effect would also increase with duration of exposure and duty cycle. In this instance, uniformity of dosage is achieved by exposure of the target region of the lumen with a sufficient amplitude combined with a duration and duty cycle to create a desired level of effect.

Alternatively, the uniform dosage can be achieved by thermal bio-effects related to the absorption of ultrasound energy, wherein the temperature rise is determined by the balance of ultrasound energy absorbed by the tissue with the thermal energy carried away by perfusion and by thermal conduction and convection. In this aspect of the invention, uniformity of dose would be achieved by the average temporal intensity of the ultrasound, with the insonification being sustained for a sufficiently long duration to heat the tissue to the desired temperature. In time, thermal equilibrium may be reached, and no further temperature rise would be seen. However, the biological effect of the ultrasonic heating may be enhanced by a longer duration of exposure to this elevated temperature. Furthermore, in conjunction with the heating of tissue due to absorption of ultrasound energy, direct heating of the ultrasonic transducer due to electromechanical losses within the device itself will also be present. Such transducer heating warms the surrounding tissues through perfusion and by way of thermal convection and conduction.

Alternatively, the uniform dosage can be achieved by radiation pressure forces arising from the absorption and reflection of ultrasound on the circumferential walls of the lumen, thereby producing a uniform effect due to the fact that the tension in the wall of the lumen will tend to be equal around its circumference. Accordingly, a uniform biological effect will occur even if there is variation in the intensity of the ultrasound (as in the case of the nonisotropic devices described herein). This is due to the fact that the tension around the circumference of the lumen will be equal in the absence of tangential forces. Radiation pressure forces arising from the present ultrasound catheter systems are primarily radial, rather than tangential, since the predominant direction of propagation of the ultrasound energy would be radial. The magnitude of the radiation pressure force achieved by the present invention is dependent on the temporal average intensity of ultrasound during the ultrasonic burst, multiplied by the ultrasound beam area. In other terms, the radiation pressure force is dependent on the temporal average power emitted during the ultrasonic burst. Adjusting the length of the burst and the pulse repetition frequency can be used to enhance the bio-effect arising from this radiation pressure. Increasing the overall duration of exposure may further enhance this bio-effect. With respect to radiation pressure forces, therefore, the present invention produces uniformity of tension around the circumference of the lumen. Uniformity of dosage is then achieved by optimal adjustment of ultrasonic power, burst length and pulse repetition frequency, and ensuring that each longitudinal segment of the artery receives the appropriate duration of exposure.

Figure 5B:
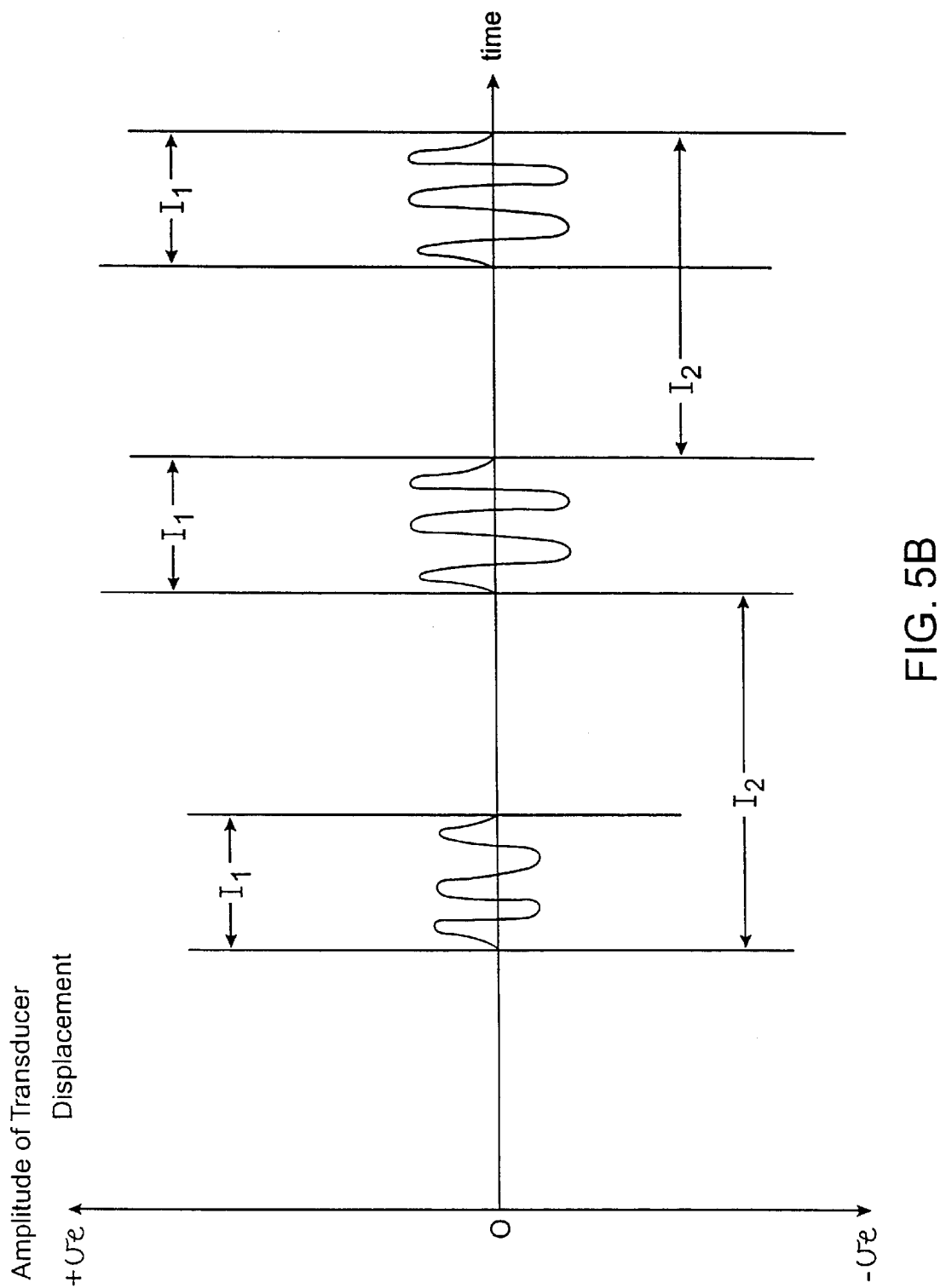

Referring to FIG. 5A, ultrasound directed outwardly in radial directions from transducer 20 in directions D1 and D2 will cause radiation pressure displacing lumen 45 outwardly from an initial rest position shown as 45a to an outwardly displaced position 45b. As lumen 45 expands to the position of 45b, a uniform tension will be created around the circumference of the lumen, regardless of the non-isotropic pattern of ultrasound from transducer 20. As is shown in FIG. 5B, transducer 20 or 60 is preferably pulsed in operation. In particular, the transducer is preferably operated during time intervals I1, wherein time intervals I1 recur at intervals of time I2. In a preferred aspect of the invention, the frequency of intervals of time I2 is selected to approximate the natural resonance frequency of the body lumen, such that the transducer causes resonance in the walls of the body lumen, (at the lower I2 frequency), while simultaneously delivering therapeutic ultrasound, (at a higher frequency during the I1 intervals of time).

Alternatively, uniform ultrasound dosage can be achieved by direct effects on cells arising from the actual ultrasound vibrations. It is likely that the extent of the bio-effect from such a mechanism would be dependent on the samplitude and on the duration of the ultrasound exposure. In this case, uniformity of exposure would be achieved by maintaining the amplitude or intensity of the ultrasound exposure for the required duration, and ensuring that every region around the circumference and along the length of the vessel receives the prescribed dose.

By translating or rotating various catheter systems of the present invention, uniform ultrasound dosage along the lumen can be achieved.

Figure 24:
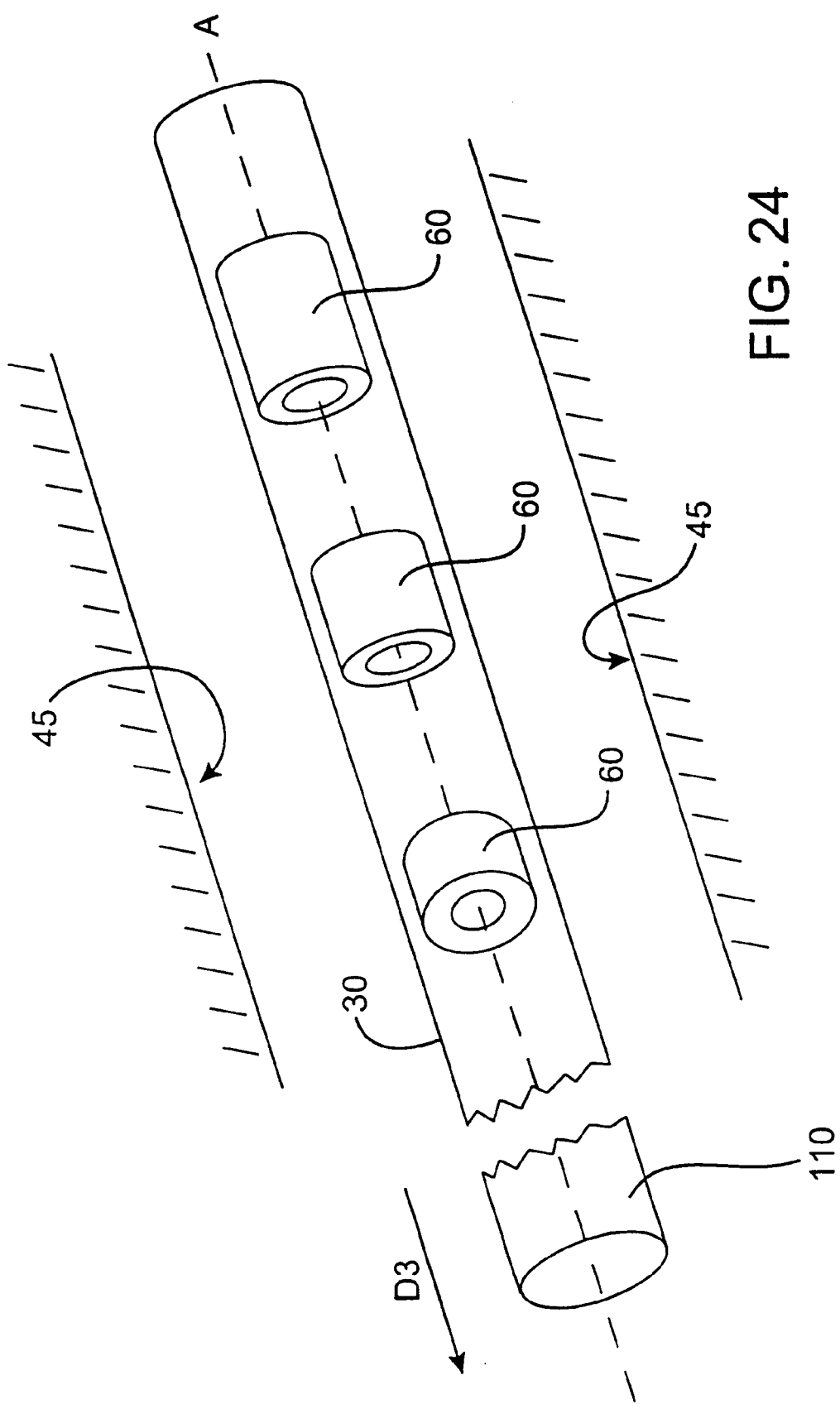
FIG. 24 is a perspective view of a plurality of isotropic transducers being axially translated along the length of a body lumen.

Referring to FIG. 24, the plurality of axially spaced apart transducers 60 (as described in FIG. 12) can be axially translated through lumen 45 at a controlled velocity by an axial translator 110. Axial translator 110 may preferably comprise a motorized pullback system. Each transducer 60 generates an isotropic radial ultrasound emission therearound. Accordingly, by translating transducers 60 at a controlled longitudinal velocity in direction D3, uniform ultrasound dosage is applied to body lumen 45.

It is to be understood that the same uniform ultrasound emission can be generated with a single isotropic transducer translated along the length of the lumen. However, when using a plurality of ultrasound transducers axially spaced apart with 50% coverage, it is only necessary to step translate the respective transducers a distance equal to one half the center-center spacing between adjacent transducers to achieve the same result.

Figure 25:
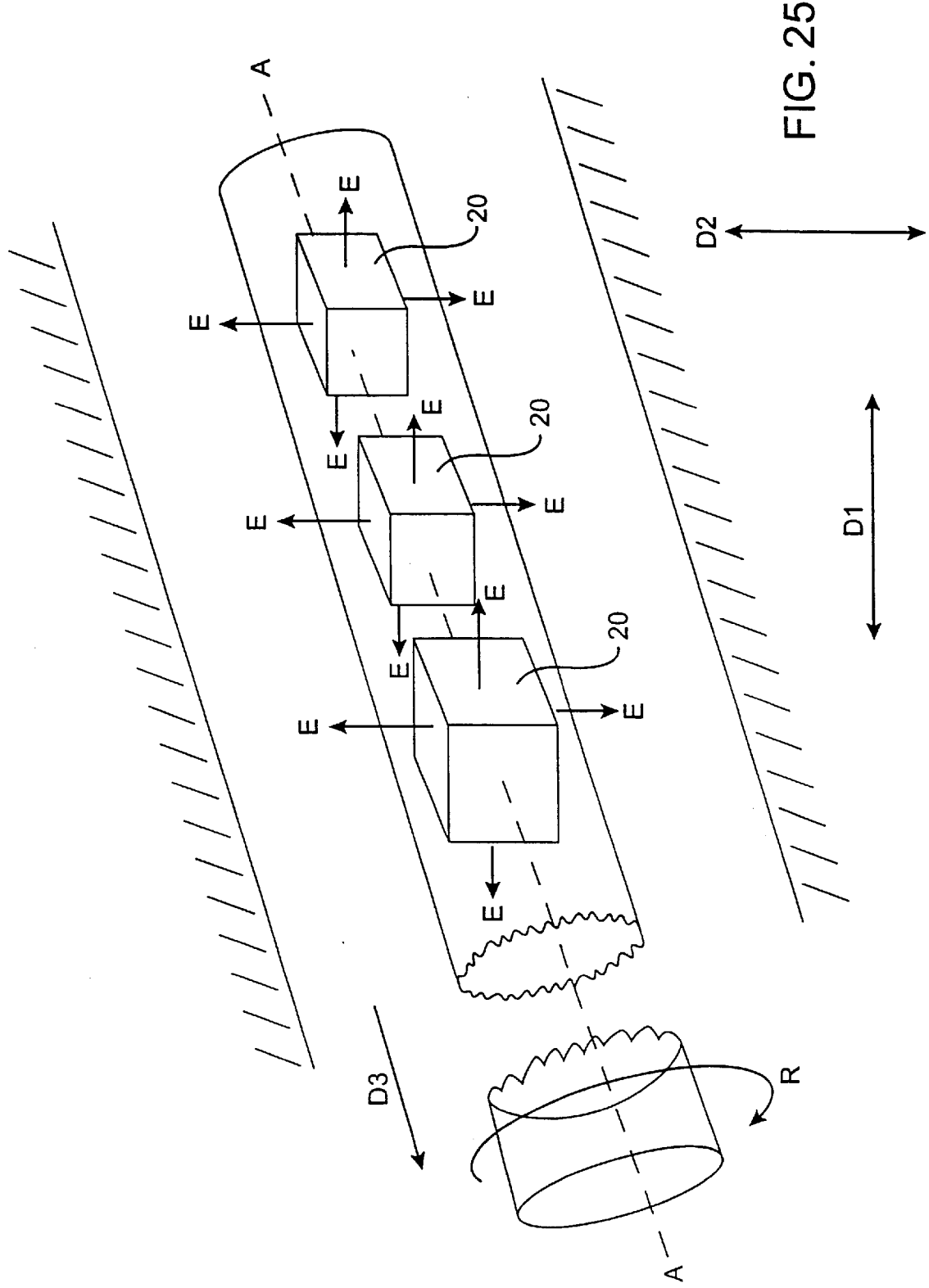
FIG. 25 is a perspective view of a plurality of non-isotropic transducers being axially translated along, and rotated within the length of a body lumen.

Referring to FIG. 25, the plurality of axially spaced apart transducers 20 (as described in FIG. 1A) can be both axially translated through lumen 45 at a controlled velocity in direction D3 and rotated in direction R about ; the central axis A of the catheter by a translation and rotation system 112. Translation and rotation system 112 may comprise a motorized pullback and rotation system.

Again, it is to be understood that the same uniform ultrasound emission can be generated with a single nonisotropic transducer translated along the length of the lumen. However, when using a plurality of ultrasound transducers which are axially spaced apart with 50% coverage, it is only necessary to step translate the respective transducers a distance equal to one half the center-to-center spacing between adjacent transducers to achieve uniform dosage.

Figure 26:
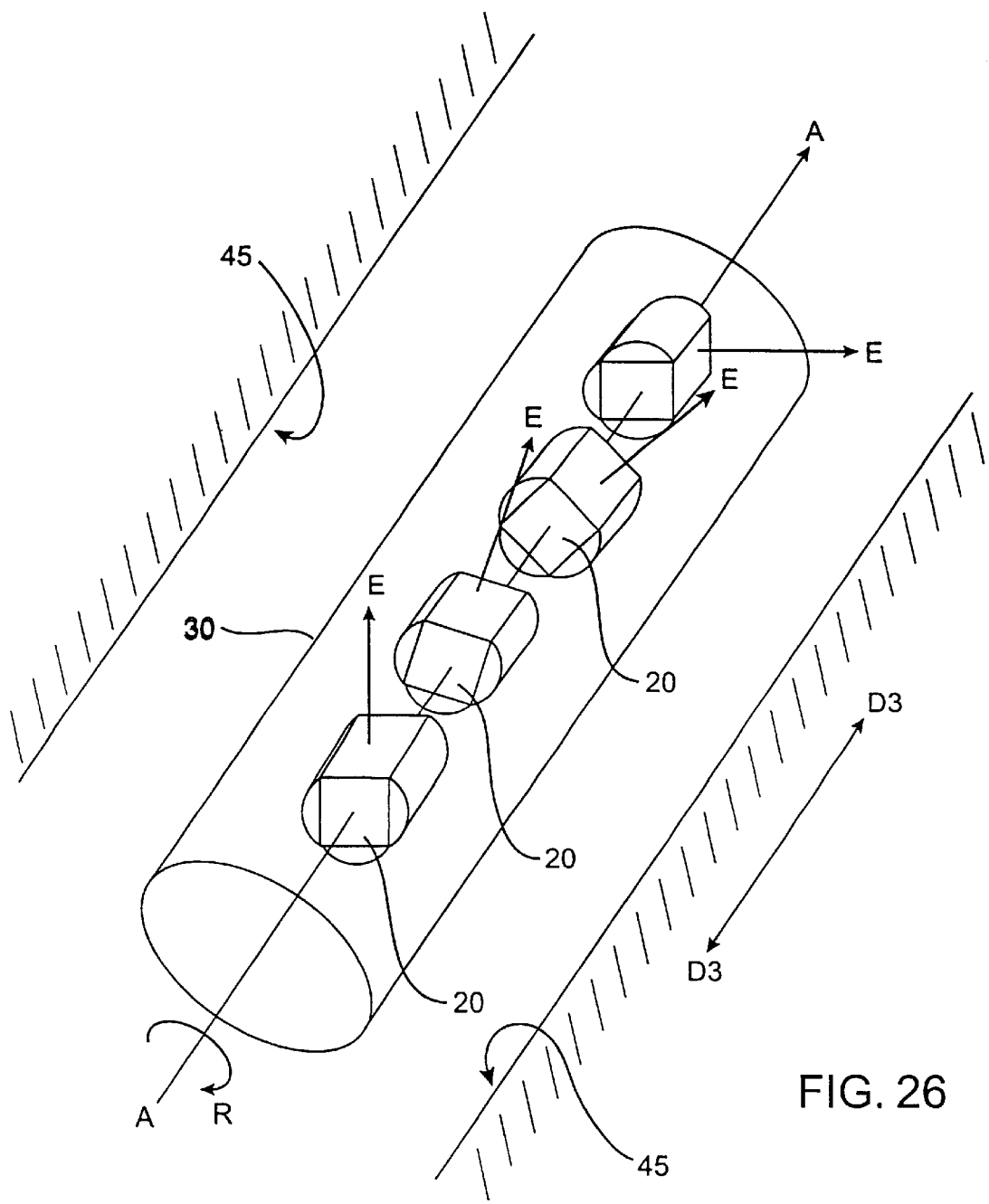
FIG. 26 is a perspective view of the system of FIG. 11 being axially translated along the length of a body lumen.

Referring to FIG. 26, (which shows the system of FIG. 11), it is possible to generate a uniform dosage of ultrasound along the length of lumen 45 by axially translating catheter 30 through the lumen. Rotation about axis A can be used to apply a more even dosage of ultrasound, but may be avoided if a sufficiently plurality of transducers 20 are included such that emissions E are radially directed sufficiently close together such that all regions of the lumen have ultrasound directed thereto as the catheter is pulled through the lumen.

Simultaneous Imaging and Therapeutic Ultrasound Delivery Systems

When operating the axial translation and simultaneous rotation system as illustrated in FIG. 25 to achieve uniform ultrasound dosage along lumen 45, it is also possible to attach an imaging transducer 120 to concurrently image the body lumen as transducers 20 are rotated about, and translated along, axis A.

Figure 27:
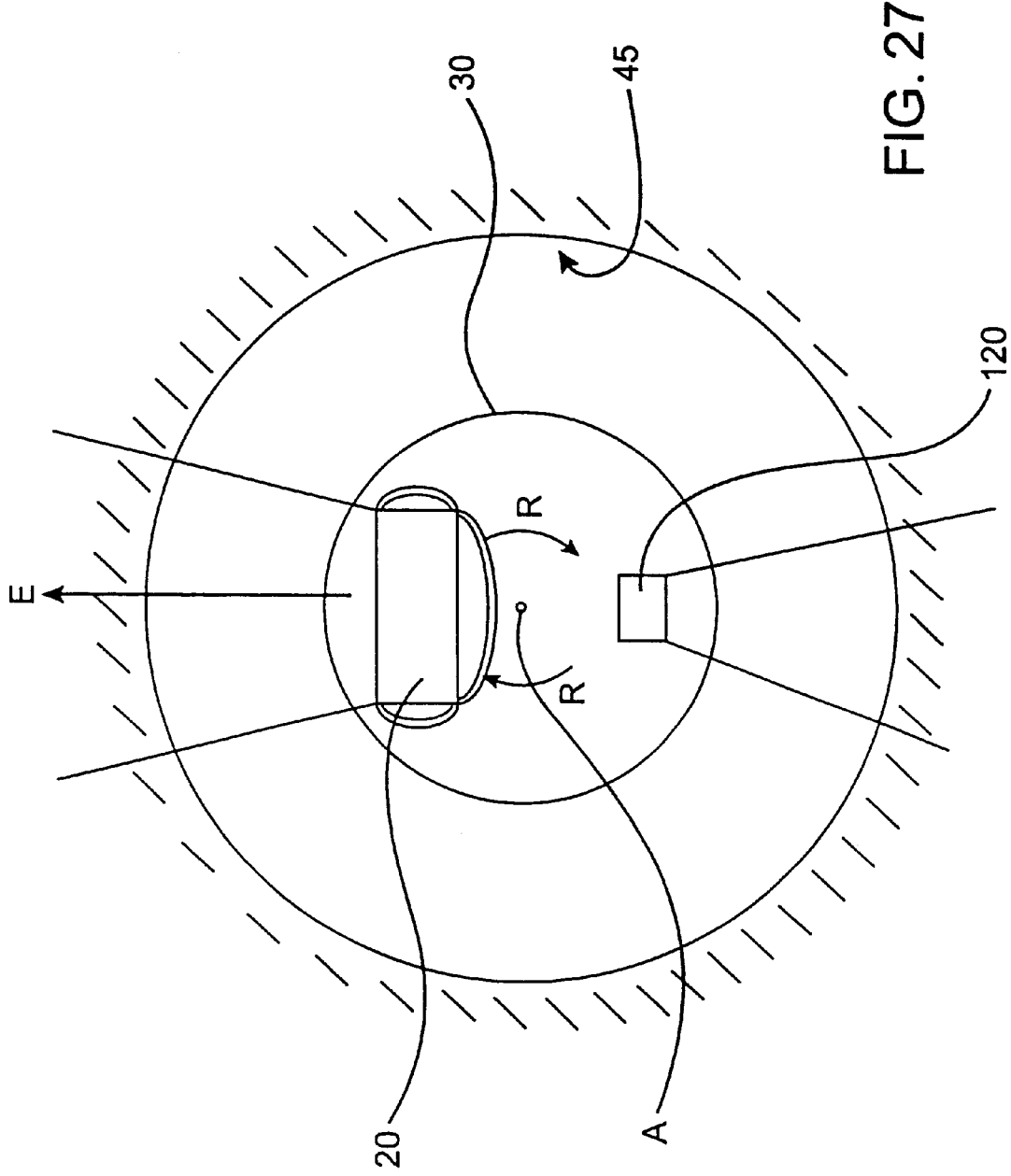
FIG. 27 is a sectional view of a simultaneous imaging and therapy ultrasound catheter system.

Referring to FIG. 27, imaging transducer 120 may comprise an IVUS transducer operating at a frequency of about 30 MHz. As transducers 20 operate at much lower frequencies, filtering of the IVUS signal will allow for simultaneous and independent operation of transducers 20 and 120. The utilization of imaging transducer 120 in close proximity with therapeutic transducers 20 will allow real time assessment of tissues during therapy.

As also shown in FIG. 27, transducer 20 may have three sides acoustically blocked so as to emit ultrasound solely in direction E.

Figure 28:
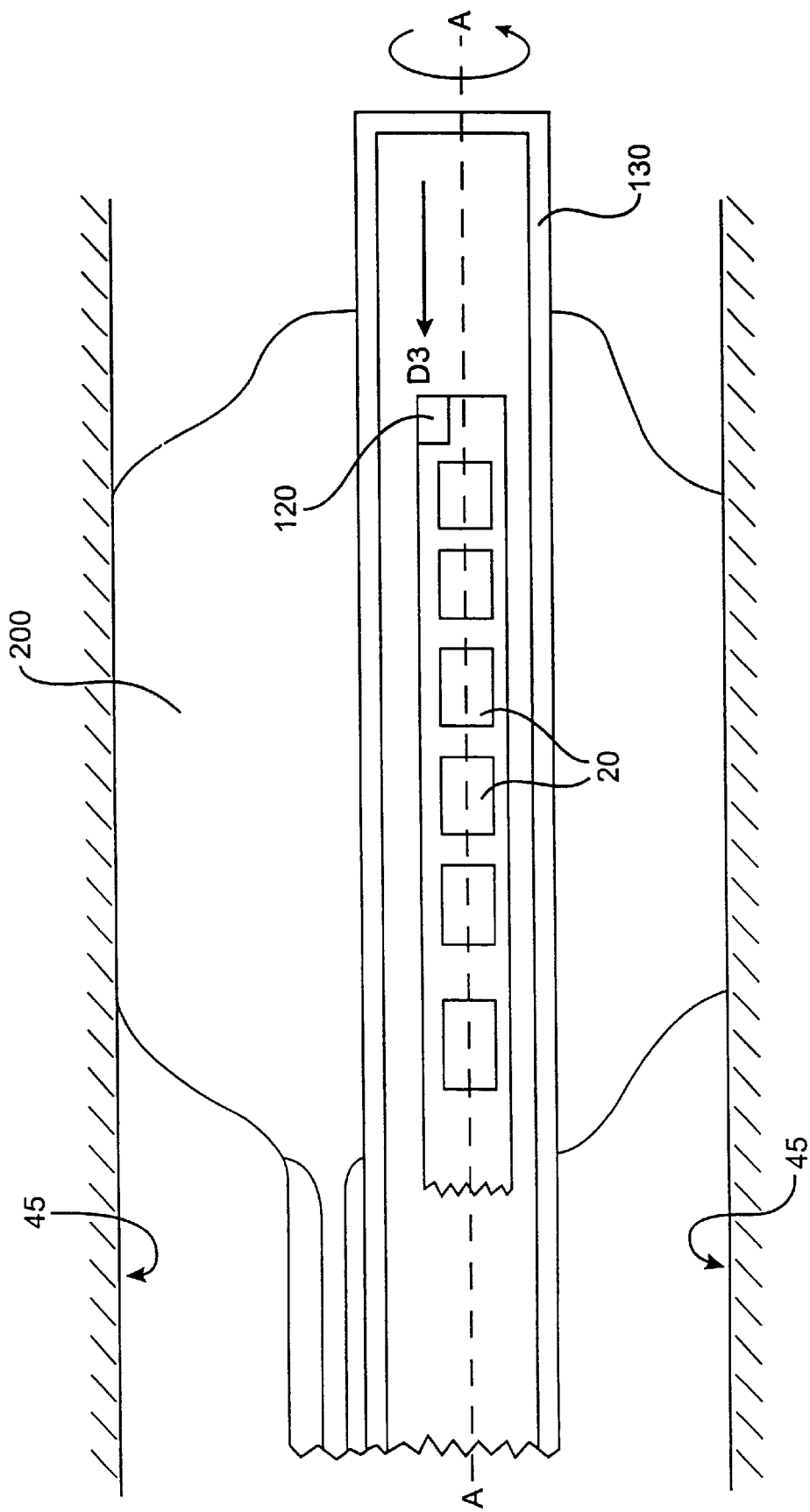
FIG. 28 is an elevation view of a simultaneous imaging and therapy ultrasound catheter system rotating and translating within a body lumen comprising a sheath separating rotating part from a stationary balloon system.

Referring to FIG. 28, a sheath 130 can be provided to separate the axially translating and rotating transducers 20 and 120 from stationary balloon system 200. It is to be understood that balloon system 200 may comprise any of the novel balloon systems set out herein, or any other balloon system, or a sheath with no balloon system.

What is claimed is:

1. A device for treating a target region in a body lumen with a uniform dose of therapeutic ultrasound energy, comprising:
   a catheter having a central axis;
   a plurality of cylindrically-shaped ultrasound transducers each having a central axis disposed parallel with the central axis of the catheter, said transducers being axially spaced apart along the central axis of the catheter, wherein each of the plurality of ultrasound transducers is adapted to deliver a therapeutic dose of ultrasound energy; and
   a translation system for moving the plurality of ultrasound transducers at a controlled velocity through the body lumen.

2. The device of claim 1, wherein, the plurality of ultrasound transducers are each fabricated from a material selected from the group consisting of a single crystal piezoelectric material, a polycrystalline piezoelectric material, an electrostrictive material, and a magnetostrictive material.

3. A device for treating a target region in a body lumen with a uniform dose of therapeutic ultrasound energy, comprising:
   a catheter having a central axis;
   a plurality of cylindrically shaped axially spaced apart transducers each having a central axis disposed parallel with the central axis of the catheter, said transducers being disposed along the central axis, wherein each of the transducers is adapted to deliver a therapeutic dose of ultrasound energy; and
   a rotation system for rotating the plurality of spaced apart ultrasound transducers at a controlled angular velocity around the central axis of the catheter.

4. The device of claim 3, further comprising,
   a translation system for moving the plurality of spaced apart ultrasound transducers at a controlled velocity in a direction parallel to the central axis of the catheter.

5. The device of claim 3, wherein, the plurality of ultrasound transducers are each fabricated from a material selected from the group consisting of a single crystal piezoelectric material, a polycrystalline piezoelectric material, an electrostrictive material, and a magnetostrictive material.

6. A device for treating a target region in a body lumen with a uniform dose of therapeutic ultrasound energy, comprising:
   a catheter having a central axis;
   an ultrasound transducer attached to the catheter, wherein said transducer is adapted to deliver a therapeutic dose of ultrasound energy;
   a translation system for moving the ultrasound transducer at a controlled velocity in a direction parallel to the central axis of the catheter; and
   a rotation system for rotating the ultrasound transducer at a controlled angular velocity about the central axis of the catheter.

7. The device of claim 6, wherein the ultrasound transducer comprises,
   a rectangular bar shaped transducer having at least two surfaces disposed parallel to the central axis acoustically insulated to block ultrasound emissions therefrom such that ultrasound energy is only emitted from at least one unblocked surface disposed parallel to the central axis of the catheter.

8. The device of claim 6, wherein, the transducer is fabricated from a material selected from the group consisting of a single crystal piezoelectric material, a polycrystalline piezoelectric material, an electrostrictive material, and a magnetostrictive material.

9. A device for treating a target region in a body lumen with a uniform dose of therapeutic ultrasound energy, comprising:

a catheter having a central axis;

a plurality of spaced apart transducers disposed along the central axis, wherein the plurality of ultrasound transducers are positioned at a separation distance less than or equal to the diameter of the catheter to generate a uniform emission along the length of a body lumen and a translation system adapted to step translate the respective transducers a distance equal to one half the center-to-center spacing between adjacent transducers.

10. A device for treating a target region in a body lumen with a uniform dose of therapeutic ultrasound energy while simultaneously imaging the target region, comprising:

a catheter having a central axis;

at least one therapeutic ultrasound transducer disposed on the catheter;

an imaging ultrasound transducer disposed on the catheter;

a rotation system for rotating the at least one therapeutic ultrasound transducer and at least one imaging ultrasound transducer at a controlled angular velocity about the central axis of the catheter; and a translation system for axially moving the at least one therapeutic ultrasound transducer and the at least one imaging ultrasound transducer at a controlled velocity through the lumen.

11. The device of claim 10, wherein, the at least one therapeutic ultrasound transducer comprises a plurality of cylindrically shaped transducers spaced apart along the central axis of the catheter.

12. The device of claim 10, wherein, the at least one therapeutic ultrasound transducer comprises a plurality of rectangular bar transducers spaced apart along the central axis of the catheter.

13. The device of claims 1, 3, 6, 9, or 10, further comprising, a distal balloon mounted to the catheter and having an inflation lumen extending through the catheter; and a proximal balloon mounted to the catheter and having an inflation lumen extending through the catheter; and an infusion port in the catheter, the infusion port having a fluid delivery lumen extending through the catheter.

14. The ultrasound delivery system of claim 13, further comprising, a flushing port in the catheter, the flushing port having a fluid delivery lumen extending through the catheter.

15. The ultrasound delivery system of claims 1, 3, 6, 9, or 10, further comprising, a balloon having distal and proximal shoulders, the balloon mounts to the catheter and having an inflation lumen extending through the catheter.

16. The ultrasound delivery system of claim 15, further comprising, an infusion port in the catheter, the infusion port having a fluid delivery lumen extending through the catheter.

17. The ultrasound delivery system of claim 15, wherein, the balloon is porous.

18. The ultrasound delivery system of claim 15, further comprising, a flushing port in the catheter, the flushing port having a fluid delivery lumen extending through the catheter.

19. The ultrasound delivery system of claim 13, further comprising, an infusion chamber disposed between the distal and proximal shoulders of the balloon, the infusion chamber surrounding the region of the balloon between the distal and proximal shoulders of the balloon.

20. The ultrasound delivery system of claims 1, 3, 6, 9, or 10, further comprising, a porous compliant balloon mounted to the catheter and having a fluid delivery lumen extending through the catheter.

21. The ultrasound delivery system of claims 1, 3, 6, 9, or 10, further comprising, a porous non-compliant balloon mounted to the catheter and having a fluid delivery lumen extending through the catheter.

22. The ultrasound delivery system of claims 13, further comprising, a sheath internal to the balloon or balloons, wherein the ultrasound transducers can be translated or rotated independent of the balloon or balloons.

23. The device of claim 11, wherein, the cylindrically shaped transducers have opposite electroded surfaces.

24. The device of claim 23, wherein, the opposite electroded surfaces are flat ends of each transducer disposed perpendicular to the central axis of the catheter.

25. The device of claim 23, wherein, the opposite electroded surfaces of each transducer are an outer curved surface and an inner curved surface defined by a longitudinally extending bore passing through the transducer.

26. The device of claim 23, further comprising, a guidewire received through a longitudinally extending bore passing through each of the plurality of transducers.

27. A device for treating a target region in a body lumen with a uniform dose of therapeutic ultrasound energy, comprising:

a catheter having a central axis; and a plurality of ultrasound transducers axially spaced apart along the central axis of the catheter wherein each of the ultrasound transducers are spaced apart by a distance not exceeding their lengths and a translation system adapted to step translate the respective transducers a distance equal to one half the center-to-center spacing between adjacent transducers.

28. The device of claim 27, herein, the plurality of ultrasound transducers comprise, cylindrical shaped transducers, each having a central axis disposed parallel with a central axis of the lumen.

29. The device of claim 27, wherein the plurality of ultrasound transducers comprise, rectangular bar shaped transducers having at least two surfaces of each transducer disposed parallel to the central axis acoustically insulated to block ultrasound emissions therefrom such that ultrasound energy is only emitted from at least one unblocked surface disposed parallel to the central axis of the catheter.

30. The device of claim 29, wherein, successive transducers are disposed at an angle to one another about the central axis of the catheter such that the transducers emit ultrasound energy in different radial directions, the different radial directions all being normal to the central axis of the catheter.

31. The device of claim wherein, the plurality of ultrasound transducers are each fabricated from a material selected from the group consisting of a single crystal piezoelectric material, a polycrystalline piezoelectric material, an electrostrictive material, and a magnetostrictive material.

32. A device for treating a target region in a body lumen with a uniform dose of therapeutic ultrasound energy, comprising:
a catheter having a central axis;
a plurality of rectangular bar shaped ultrasound transducers axially spaced apart along the central axis of the catheter, each transducer having at least two surfaces of each transducer disposed parallel to the central axis acoustically insulated to block ultrasound emissions therefrom such that ultrasound energy is only emitted from at least one unblocked surface disposed parallel to the central axis of the catheter, and wherein successive transducers are disposed at an angle to one another about the central axis of the catheter such that the transducers emit ultrasound energy in different radial directions, the different radial directions all being normal to the central axis of the catheter; and
a translation system for moving the plurality of ultrasound transducers at a controlled velocity through the body lumen.

33. A device for treating a target region in a body lumen with a uniform dose of therapeutic ultrasound energy, comprising:
a catheter having a central axis;
a plurality of spaced apart transducers disposed along the central axis at a separation distance less than or equal to the diameter of the catheter to generate a uniform emission along the length of a body lumen; and
a rotation system for rotating the plurality of spaced apart ultrasound transducers at a controlled angular velocity around the central axis of the catheter.

34. A device for treating a target region in a body lumen with a uniform dose of therapeutic ultrasound energy, comprising:
a catheter having a central axis;
a plurality of ultrasound transducers axially spaced apart along the central axis of the catheter;
a translation system for moving the plurality of ultrasound transducers at a controlled velocity through the body lumen;
a distal balloon mounted to the catheter and having an inflation lumen extending through the catheter;
a proximal balloon mounted to the catheter and having an inflation lumen extending through the catheter; and
an infusion port in the catheter, the infusion port having a fluid delivery lumen extending through the catheter.

35. The ultrasound delivery system of claim 34, further comprising,
a flushing port in the catheter, the flushing port having a fluid delivery lumen extending through the catheter.

36. A device for treating a target region in a body lumen with a uniform dose of therapeutic ultrasound energy, comprising:
a catheter having a central axis;
a plurality of ultrasound transducers axially spaced apart along the central axis of the catheter;
a translation system for moving the plurality of ultrasound transducers at a controlled velocity through the body lumen; and
a balloon having distal and proximal shoulders, the balloon mounted to the catheter and having an inflation lumen extending through the catheter.

37. The device of claim 36, farther comprising:
an infusion port in the catheter, the infusion port having a fluid delivery lumen extending through the catheter.

38. The device of claim 36, wherein the balloon is porous.

39. The device of claim 36, further comprising,
a flushing port in the catheter, the flushing port having a fluid delivery lumen extending through the catheter.

40. The device of claim, further comprising,
an infusion chamber disposed between the distal and proximal shoulders of the balloon, the infusion chamber surrounding the region of the balloon between the distal and proximal shoulders of the balloon.

41. A device for treating a target region in a body lumen with a uniform dose of therapeutic ultrasound energy, comprising:
a catheter having a central axis;
a plurality of ultrasound transducers axially spaced apart along the central axis of the catheter;
a translation system for moving the plurality of ultrasound transducers at a controlled velocity through the body lumen; and
a porous compliant balloon mounted to the catheter and having a fluid delivery lumen extending through the catheter.

42. A device for treating a target region in a body lumen with a uniform dose of therapeutic ultrasound energy, comprising:
a catheter having a central axis;
a plurality of ultrasound transducers axially spaced apart along the central axis of the catheter;
a translation system for moving the plurality of ultrasound transducers at a controlled velocity through the body lumen; and
a porous non-compliant balloon mounted to the catheter and having a fluid delivery lumen extending through the catheter.

43. The device of claim 34, further comprising:
a sheath internal to the balloon or balloons, wherein the ultrasound transducers can be translated or rotated independent of the balloon or balloons.

44. A device for treating a target region in a body lumen with a uniform dose of therapeutic ultrasound energy, comprising:
a catheter having a central axis;
a plurality of cylindrical shaped ultrasound transducers axially spaced apart along the central axis of the catheter, each having a central axis disposed parallel with a central axis of the lumen, and each having opposite electroded surfaces; and
a translation system for moving the plurality of ultrasound transducers at a controlled velocity through the body lumen.

45. The device of claim 44, wherein,
the opposite electroded surfaces are flat ends of each transducer disposed perpendicular to the central axis of the catheter.

46. The device of claim 44, wherein,
the opposite electroded surfaces of each transducer are an outer curved surface and an inner curved surface defined by a longitudinally extending bore passing through the transducer.

47. The device of claim 44, a further comprising,
a guidewire received through a longitudinally extending bore passing through each of the plurality of transducers.

48. A device for treating a target region in a body lumen with a uniform dose of therapeutic ultrasound energy, comprising:

a catheter having a central axis;

a plurality of spaced apart transducers disposed along the central axis;

a rotation system for rotating the plurality of spaced apart ultrasound transducers at a controlled angular velocity around the central axis of the catheter;

a distal balloon mounted to the catheter and having an inflation lumen extending through the catheter;

a proximal balloon mounted to the catheter and having an inflation lumen extending through the catheter; and an infusion port in the catheter, the infusion port having a fluid delivery lumen extending through the catheter.

49. The device of claim 48, further comprising, a flushing port in the catheter, the flushing port having a fluid delivery lumen extending through the catheter.

50. A device for treating a target region in a body lumen with a uniform dose of therapeutic ultrasound energy, comprising:

a catheter having a central axis;

a plurality of spaced apart transducers disposed along the central axis;

a rotation system for rotating the plurality of spaced apart ultrasound transducers at a controlled angular velocity around the central axis of the catheter; and a balloon having distal and proximal shoulders, the balloon mounted to the catheter and having an inflation lumen extending through the catheter.

51. The device of claim 50, further comprising, an infusion port in the catheter, the infusion port having a fluid delivery lumen extending through the catheter.

52. The device of claim 50, wherein the balloon is porous.

53. The device of claim 50, further comprising, a flushing port in the catheter, the flushing port having a fluid delivery lumen extending through the catheter.

54. The device of claim 48, further comprising, an infusion chamber disposed between the distal and proximal shoulders of the balloon, the infusion chamber surrounding the region of the balloon between the distal and proximal shoulders of the balloon.

55. The device of claim 48, further comprising, a sheath internal to the balloon or balloons, wherein the ultrasound transducers can be translated or rotated independent of the balloon or balloons.

56. A device for treating a target region in a body lumen with a uniform dose of therapeutic ultrasound energy, comprising:

a catheter having a central axis;

a plurality of spaced apart transducers disposed along the central axis;

a rotation system for rotating the plurality of spaced apart ultrasound transducers at a controlled angular velocity around the central axis of the catheter; and a porous compliant balloon mounted to the catheter and having a fluid delivery lumen extending through the catheter.

57. A device for treating a target region in a body lumen with a uniform dose of therapeutic ultrasound energy, comprising:

a catheter having a central axis;

a plurality of spaced apart transducers disposed along the central axis;

a rotation system for rotating the plurality of spaced apart ultrasound transducers at a controlled angular velocity around the central axis of the catheter; and a porous non-compliant balloon mounted to the catheter and having a fluid delivery lumen extending through the catheter.

58. A device for treating a target region in a body lumen with a uniform dose of therapeutic ultrasound energy while simultaneously imaging the target region, comprising:

a catheter having a central axis;

a plurality of cylindrically shaped transducers spaced apart along the central axis of the catheter, the transducers having opposite electroded surfaces;

an imaging ultrasound transducer disposed on the catheter;

a rotation system for rotating the at least one therapeutic ultrasound transducer and at least one imaging ultrasound transducer at a controlled angular velocity about the central axis of the catheter; and a translation system for axially moving the at least one therapeutic ultrasound transducer and the at least one imaging ultrasound transducer at a controlled velocity through the lumen.

59. The device of claim 58, wherein, the opposite electroded surfaces are flat ends of each transducer disposed perpendicular to the central axis of the catheter.

60. The device of claim 58, wherein, the opposite electroded surfaces of each transducer are an outer curved surface and an inner curved surface defined by a longitudinally extending bore passing through the transducer.

61. The device of claim 58, further comprising, a guidewire received through a longitudinally extending bore passing through each of the plurality of transducers.

62. A device for treating a target region in a body lumen with a uniform dose of therapeutic ultrasound energy, comprising:

a catheter having a central axis;

a plurality of spaced apart transducers disposed along the central axis, wherein the plurality of ultrasound transducers are positioned at a separation distance less than or equal to the diameter of the catheter to generate a uniform emission along the length of a body lumen;

a distal balloon mounted to the catheter and having an inflation lumen extending through the catheter;

a proximal balloon mounted to the catheter and having an inflation lumen extending through the catheter; and an infusion port in the catheter, the infusion port having a fluid delivery lumen extending through the catheter.

63. The device of claim 62, further comprising, a flushing port in the catheter, the flushing port having a fluid delivery lumen extending through the catheter.

64. A device for treating a target region in a body lumen with a uniform dose of therapeutic ultrasound energy, comprising:

a catheter having a central axis;

a plurality of spaced apart transducers disposed along the central axis, wherein the plurality of ultrasound transducers are positioned at a separation distance less than or equal to the diameter of the catheter to generate a uniform emission along the length of a body lumen;

a balloon having distal and proximal shoulders, the balloon mounted to the catheter and having an inflation lumen extending through the catheter.

65. The device of claim 64, further comprising an infusion port in the catheter, the infusion port having a fluid delivery lumen extending through the catheter.

66. The device of claim 64, wherein, the balloon is porous.

67. The device of claim 64, further comprising, a flushing port in the catheter, the flushing port having a fluid delivery lumen extending through the catheter.

68. The device of claim 62, further comprising, an infusion chamber disposed between the distal and proximal shoulders of the balloon, the infusion chamber surrounding the region of the balloon between the distal and proximal shoulders of the balloon.

69. A device for treating a target region in a body lumen with a uniform dose of therapeutic ultrasound energy, comprising:

a catheter having a central axis;

a plurality of spaced apart transducers disposed along the central axis, wherein the plurality of ultrasound transducers are positioned at a separation distance less than or equal to the diameter of the catheter to generate a uniform emission along the length of a body lumen; and a porous compliant balloon mounted to the catheter and having a fluid delivery lumen extending through the catheter.

70. A device for treating a target region in a body lumen with a uniform dose of therapeutic ultrasound energy, comprising:

a catheter having a central axis;

a plurality of spaced apart transducers disposed along the central axis, wherein the plurality of ultrasound transducers are positioned at a separation distance less than or equal to the diameter of the catheter to generate a uniform emission along the length of a body lumen; and a porous non-compliant balloon mounted to the catheter and having a fluid delivery lumen extending through the catheter.

71. The device of claim 62, further comprising, a sheath internal to the balloon or balloons, wherein the ultrasound transducers can be translated or rotated independent of the balloon or balloons.

* * * * *